(12) United States Patent
Booth et al.

(10) Patent No.: US 9,290,807 B2
(45) Date of Patent: Mar. 22, 2016

(54) METHODS FOR DETECTION OF NUCLEOTIDE MODIFICATION

(75) Inventors: Michael John Booth, Cambridge (GB); Shankar Balasubramanian, Cambridge (GB)

(73) Assignee: Cambridge Epigenetix Limited, Cambourne (GB)

( * ) Notice: Subject to any disclaimer, the term of this patent is extended or adjusted under 35 U.S.C. 154(b) by 0 days.

(21) Appl. No.: 14/235,707

(22) PCT Filed: Jul. 27, 2012

(86) PCT No.: PCT/GB2012/051819
§ 371 (c)(1),
(2), (4) Date: Jan. 28, 2014

(87) PCT Pub. No.: WO2013/017853
PCT Pub. Date: Feb. 7, 2013

(65) Prior Publication Data
US 2014/0178881 A1   Jun. 26, 2014

Related U.S. Application Data

(60) Provisional application No. 61/513,356, filed on Jul. 29, 2011, provisional application No. 61/605,702, filed on Mar. 1, 2012, provisional application No. 61/623,461, filed on Apr. 12, 2012, provisional application No. 61/641,134, filed on May 1, 2012.

(51) Int. Cl.
*C12Q 1/68*   (2006.01)

(52) U.S. Cl.
CPC ............ *C12Q 1/6876* (2013.01); *C12Q 1/6827* (2013.01)

(58) Field of Classification Search
None
See application file for complete search history.

(56) References Cited

U.S. PATENT DOCUMENTS

2007/0037184 A1*  2/2007  Boyd et al. .................. 435/6

FOREIGN PATENT DOCUMENTS

EP    0377521 A1    7/1990
EP    0652321 A1    5/1995

(Continued)

OTHER PUBLICATIONS

Bentley et al., "Accurate Whole Human Genome Sequencing Using Reversible Terminator Chemistry", Nature, vol. 456, pp. 53-59 (2008).

(Continued)

*Primary Examiner* — Robert T Crow
(74) *Attorney, Agent, or Firm* — Klauber & Jackson LLC

(57) ABSTRACT

This invention relates to the identification of modified cytosine residues, such as 5-methylcytosine (5mC), 5-hydroxymethylcytosine (5hmC) and 5-formylcytosine (5fC) to be distinguished from cytosine (C) in a sample nucleotide sequence. Methods may comprise oxidizing or reducing a first portion of polynucleotides which comprise the sample nucleotide sequence; treating the oxidized or reduced first portion and a second portion of polynucleotides with bisulfite; sequencing the polynucleotides in the first and second portions of the population following steps ii) and iii) to produce first and second nucleotide sequences, respectively and; identifying the residue in the first and second nucleotide sequences which corresponds to a cytosine residue in the sample nucleotide sequence. These methods may be useful, for example in the analysis of genomic DNA and/or of RNA.

27 Claims, 20 Drawing Sheets

(56) References Cited

FOREIGN PATENT DOCUMENTS

| WO | WO-9218134 A1 | 10/1992 | |
|---|---|---|---|
| WO | WO 2009/049916 A2 * | 4/2009 | C12Q 1/68 |

OTHER PUBLICATIONS

Borgel et al., "Targets and Dynamics of Promoter DNA Methylation During Early Mouse Development," Nature Genetics, vol. 42, pp. 1093-1101 (2010).
Branco et al., "Uncovering the Role of 5-Hydroxymethylcytosine in the Epigenome," Nature Reviews Genetics, vol. 13, pp. 7-13 (2012).
Deaton et al., "CpG Islands and the Regulation of Transcription," Genes & Development, vol. 25, pp. 1010-1022 (2011).
Eid et al., "Real-Time DNA Sequencing from Single Polymerase Molecules," Science, vol. 323, pp. 133-138 (2009).
Ficz et al., "Dynamic Regulation of 5-Hydroxymethylcytosine in Mouse ES Cells and During Differentiation," Nature, vol. 473, pp. 398-404 (2011).
Flusberg et al., "Direct Detection of DNA Methylation During Single-molecule, Real-time Sequencing," Nature Methods, vol. 7. pp. 461-465 (2010).
Frommer et al., "A Genomic Sequencing Protocol that Yields a Positive Display of 5-Methylcytosine Residues in Individual DNA Strands," Proc. Natl. Acad. Sci., vol. 89, pp. 1827-1831 (1992).
Goodier et al., "A Novel Active L1 Retrotransposon Subfamily in the Mouse," Genome Research, vol. 11, pp. 1677-1685 (2001).
Green et al., "Oxo Complexes of Ruthenium(VI) and (VII) as Organic Oxidants," J. Chem. Soc., pp. 681-686 (1984).
Gu et al., "Preparation of Reduced Representation Bisulfite Sequencing Libraries for Genome-scale DNA Methylation Profiling," Nature Protocols, vol. 6, pp. 468-481 (2011).
Gupta et al., "Advances in Genome-wide DNA Methylation Analysis," Biotechniques, vol. 49, pp. iii-xi (2010).
Hayatsu et al., "Accelerated Bisulfite-deamination of Cytosine in the Genomic Sequencing Procedure for DNA Methylation Analysis," Nucleic Acids Symposium Series No. 48, pp. 261-262 (2004).
Huang et al., "The Behaviour of 5-Hydroxymethylcytosine in Bisulfite Sequencing," PLoS One, vol. 5, e8888, pp. 1-9 (2010).
Illingworth et al., "Orphan CpG Islands Identify Numerous Conserved Promoters in the Mammalian Genome," PLoS Genetics, vol. 6, pp. 1-15 (2010).
International Search Report for International Application No. PCT/GB2012/051819 dated Feb. 14, 2013; 3 pages.
Ito et al., "Role of Tet Proteins in 5mC to 5hmC Conversion, ES Cell Self-Renewal, and ICM Specification," Nature, vol. 466, pp. 1129-1133 (2010).
Jin et al., "Genomic Mapping of 5-Hydroxymethylcytosine in the Human Brain," Nucleic Acids. Research, vol. 39, pp. 5015-5024 (2011).
Kinney et al., "Tissue-Specific Distribution and Dynamic Changes of 5-Hydroxymethylcytosine in Mammalian Genomes," J. Biol. Chem. vol. 286, pp. 24685-24693 (2011).
Koh et al., "Tet1 and Tet2 Regulate 5-Hydroxymethylcytosine Production and Cell Lineage Specification in Mouse Embryonic Stem Cells," Cell Stem Cell, vol. 8, pp. 200-213 (2011).
Korlach et al., "Real-Time DNA Sequencing from Single Polymerase Molecules," Methods in Enzymology, vol. 472, pp. 431-455 (2010).
Kriaucionis et al., "The Nuclear DNA Base, 5-Hydroxymethylcytosine is Present in Brain and Enriched in Purkinje Neurons," Science, vol. 324, pp. 929-930 (2009).
Krueger et al., "Bismark: A Flexible Aligner and Methylation Caller for Bisulfite-Seq Applications," Bioinformatics, vol. 27, pp. 1571-1572 (2011).
Krueger et al., "Large Scale Loss of Data in Low-Diversity Illumina Sequencing Libraries Can Be Recovered by Deferred Cluster Calling," PLoS One, vol. 6, e16607, pp. 1-7 (2011).
Lane et al., "Resistance of IAPs to Methylation Reprogramming May Provide a Mechanism for Epigenetic Inheritance in the Mouse," Genesis, vol. 35, pp. 88-93 (2003).
Li et al., "Distribution of 5-Hydroxymethylcytosine in Different Human Tissues," Journal of Nucleic Acids, Article ID 870726, pp. 1-5 (2011).
Lister et al., "Highly Integrated Single-Base Resolution Maps of the Epigenome in Arabidopsis," Cell, vol. 133, pp. 523-536 (2008).
Lister et al., "Human DNA Methylomes at Base Resolution Show Widespread Epigenomic Differences," Nature, vol. 462, pp. 315-322 (2009).
McKernan et al., "Sequence and Structural Variation in a Human Genome Uncovered by Short-Read, Massively Parallel Ligation Sequencing Using Two-Base Encoding," Genome Researc, vol. 19, pp. 1527-1541 (2009).
Meissner et al., "Genome-Scale DNA Methylation Maps of Pluripotent and Differentiated Cells," Nature, vol. 454, pp. 766-770 (2008).
Munzel et al., "Quantification of the Sixth DNA Base Hydroxymethylcytosine in the Brain," Angewandte Chemie, vol. 49, pp. 5375-5377 (2010).
Nestor et al., "Enzymatic Approaches and Bisulfite Sequencing Cannot Distinguish Between 5-Methylcytosine and 5-Hydroxymethylcytosine in DNA," Biotechniques, vol. 48, pp. 317-319 (2010).
Nomura et al., "Discrimination Between 5-Hydroxymethylcytosine and 5-Methylcytosine by a Chemically Designed Peptide," Chemical Communications, vol. 47, pp. 8277-8279 (2011).
Pastor et al., "Genome-Wide Mapping of 5-Hydroxymethylcytosine in Embryonic Stem Cells," Nature, vol. 473, pp. 394-397 (2011).
Pfaffeneder et al., "The Discovery of 5-Formylcytosine in Embryonic Stem Cell DNA," Angew. Chem. Int. Ed., vol. 50, pp. 7008-7012 (2011).
Qin et al., "Intracisternal A Particle Genes: Distribution in the Mouse Genome, Active Subtypes, and Potential Roles as Species-Specific Mediators of Susceptibility to Cancer," Molecular Carcinogenesis, vol. 49, pp. 54-67 (2010).
Quinlivan et al., "DNA Digestion to Deoxyribonucleoside: A Simplified One-Step Procedure," Anal. Biochem. vol. 373, pp. 383-385 (2008).
Ronaghi et al., "A Sequencing Method Based on Real-Time Pyrophosphate," Science, vol. 281, pp. 363-365 (1998).
Rothberg et al., "An Integrated Semiconductor Device Enabling Non-Optical Genome Sequencing," Nature, vol. 475, pp. 348-352 (2011).
Sanger et al., "DNA Sequencing with Chain-Terminating Inhibitors," Proc. Natl. Acad. Sci., vol. 74, pp. 5463-5467 (1977).
Schichman et al., "L1 A-Monomer Tandem Arrays Have Expanded During the Course of Mouse L1 Evolution," Mol. Biol. Evol., vol. 10, pp. 552-570 (1993).
Song et al., "Selective Chemical Labeling Reveals the Genome-wide Distribution of 5-Hydroxymethylcytosine," Nat. Biotechnol, vol. 29, pp. 68-72 (2011).
Song et al., "Sensitive and Specific Single-Molecule Sequencing of 5-Hydroxymethylcytosine," Nat. Methods, vol. 9, pp. 75-77 (2011).
Stadler et al., "DNA-Binding Factors Shape the Mouse Methylome at Distal Regulatory Regions," Nature, vol. 480, pp. 490-495 and Corrigendum in Nature, vol. 484, p. 550 (2011).
Szwagierczak et al., "Sensitive Enzymatic Quantification of 5-Hydroxymethylcytosine in Genomic DNA," Nucleic Acids Research, vol. 38, pp. 1-5 (2010).
Tahiliani et al., "Conversion of 5-Methylcytosine to 5-Hydroxymethylcytosine in Mammalian DNA by MLL Partner TET1," Science, vol. 324, pp. 930-935 (2009).
Wallace et al., Identification of Epigenetic DNA Modifications with a protein Nanopore, Chem. Comm., vol. 46, pp. 8195-8197 (2010).
Wang et al., "Comparison of Bisulfite Modification of 5-Methyldeoxycytidine and Deoxycytidine Residues," Nucleic Acids Research, vol. 8, pp. 4777-4790 (1980).
Wanunu et al., "Discrimination of Methylcytosine from Hydroxymethylcytosine in DNA Molecules," J. Am. Chem. Soc., vol. 133, pp. 486-492 (2011).
Williams et al., "Tet1 and Hydroxymethylcytosine in Transcription and DNA Methylation Fidelity," Nature, vol. 473, pp. 343-348 (2011).
Wu et al., "Genome-wide Analysis of 5-Hydroxymethylcytosine Distribution Reveals its Dual Function in Transcriptional Regulation in Mouse Embryonic Stem Cells," Genes & Development, vol. 25, pp. 679-684 (2011).
Xu et al., "Genome-Wide Regulation of 5hmC, 5mC and Gene Expression by Tet1 Hydroxylase in Mouse Embryonic Stem Cells," Mol. Cell, vol. 42, pp. 451-464 (2011).

* cited by examiner

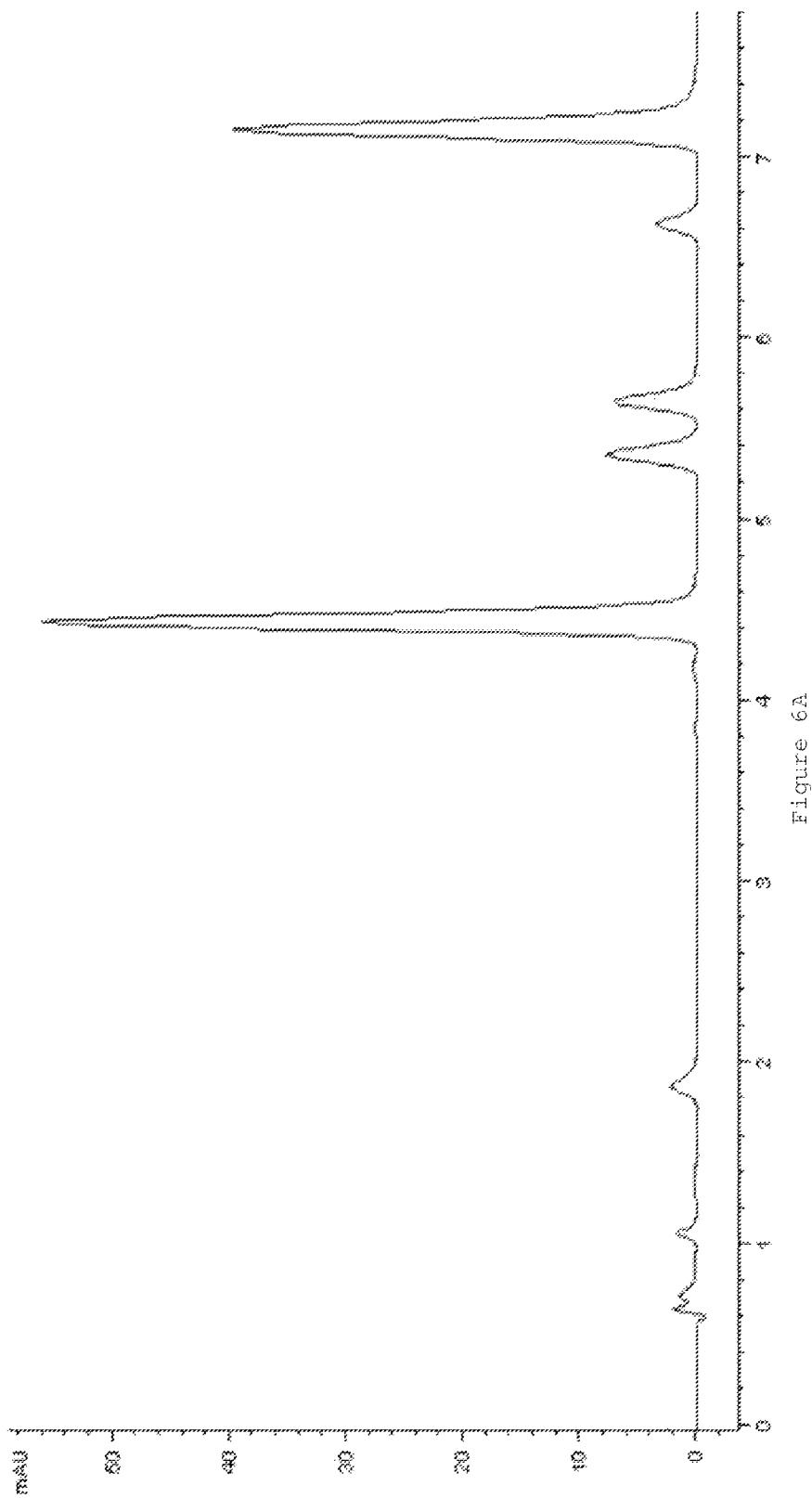

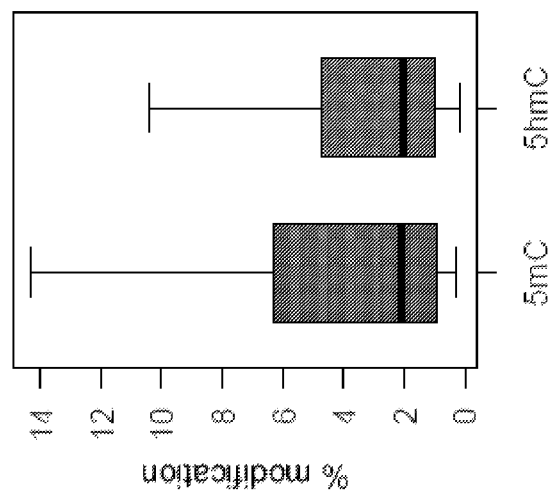
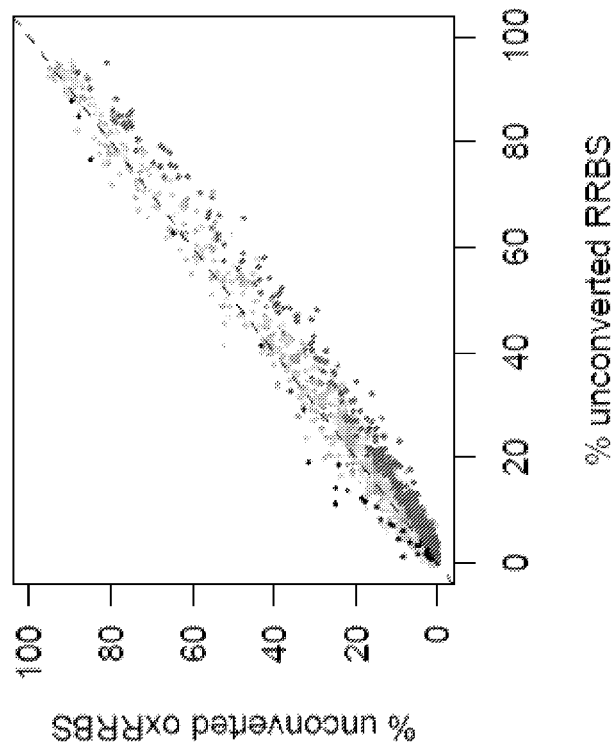
Figure 9B
Figure 9A

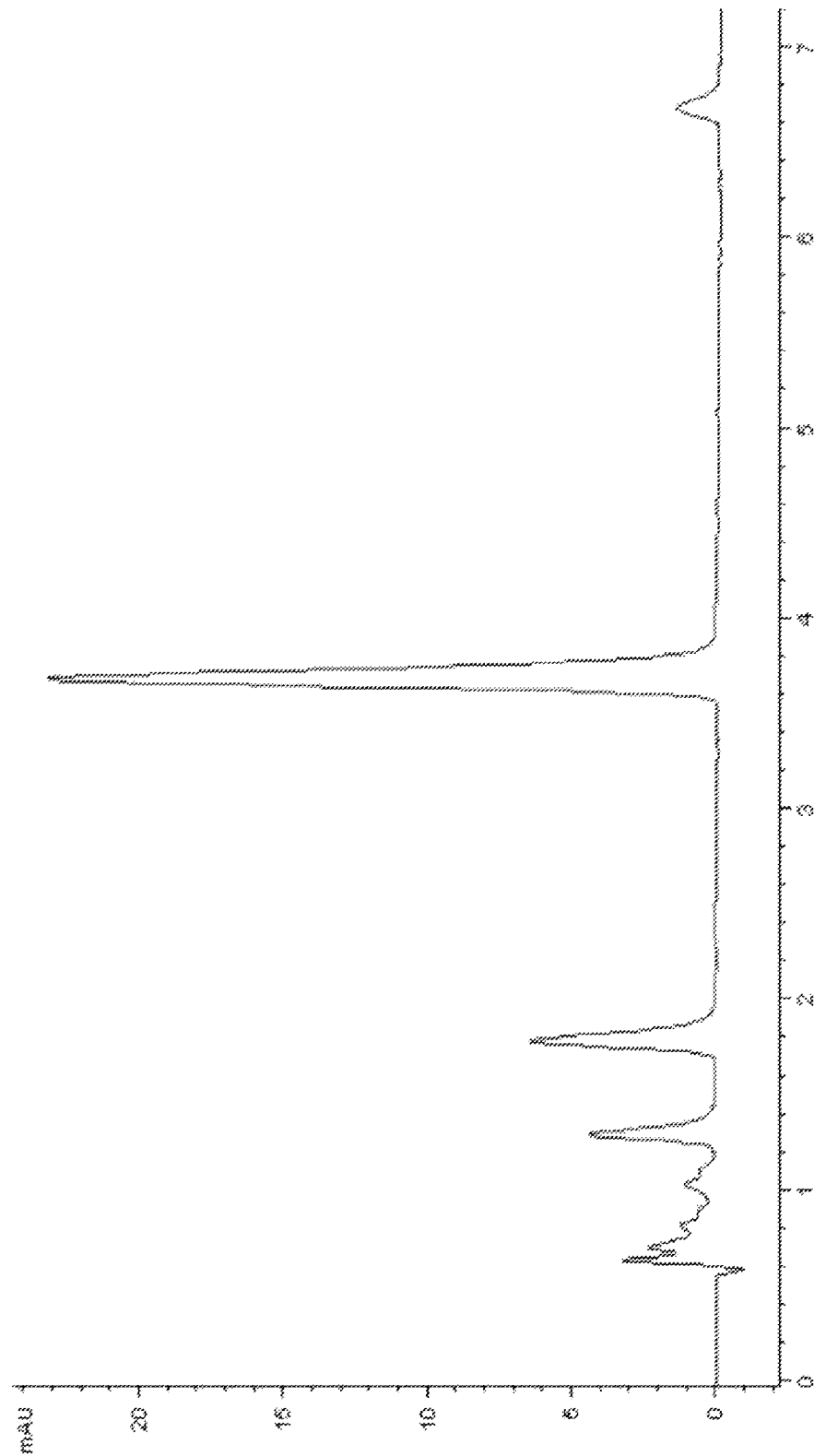

METHODS FOR DETECTION OF NUCLEOTIDE MODIFICATION

CROSS REFERENCE TO RELATED APPLICATIONS

This application is the national stage of International (PCT) Patent Application No. PCT/GB2012/051819, filed Jul. 27, 2012, and published under PCT Article 21(2) in English, which claims the benefit of and priority to U.S. Provisional Application No. 61/513,356, filed Jul. 29, 2011; U.S. Provisional Application No. 61/605,702, filed Mar. 1, 2012; U.S. Provisional Application No. 61/623,461, filed Apr. 12, 2012; and U.S. Provisional Application No. 61/641,134, filed May 1, 2012; the disclosures of each application are hereby incorporated by reference in their entirety.

This invention relates to the detection of modified cytosine residues and, in particular, to the sequencing of nucleic acids that contain modified cytosine residues.

5-methylcytosine (5mC) is a well-studied epigenetic DNA mark that plays important roles in gene silencing and genome stability, and is found enriched at CpG dinucleotides (1). In metazoa, 5mC can be oxidised to 5-hydroxymethylcytosine (5hmC) by the ten-eleven translocation (TET) family of enzymes (2, 3). The overall levels of 5hmC are roughly 10-fold lower than those of 5mC and vary between tissues (4). Relatively high quantities of 5hmC (~0.4% of all cytosines) are present in embryonic stem (ES) cells, where 5hmC has been suggested to have a role in the establishment and/or maintenance of pluripotency (2, 3, 5-9). 5hmC has been proposed as an intermediate in active DNA demethylation, for example by deamination or via further oxidation of 5hmC to 5-formylcytosine (5fC) and 5-carboxycytosine (5cC) by the TET enzymes, followed by base excision repair involving thymine-DNA glycosylase (TDG) or failure to maintain the mark during replication (10). However, 5hmC may also constitute an epigenetic mark per se.

It is possible to detect and quantify the level of 5hmC present in total genomic DNA by analytical methods that include thin layer chromatography and tandem liquid chromatography-mass spectrometry (2, 11, 12). Mapping the genomic locations of 5hmC has thus far been achieved by enrichment methods that have employed chemistry or antibodies for 5hmC-specific precipitation of DNA fragments that are then sequenced (6-8, 13-15). These pull-down approaches have relatively poor resolution (10s to 100s of nucleotides) and give only relative quantitative information that is likely to be subject to distributional biasing during the enrichment. Quantifiable single nucleotide sequencing of 5mC has been performed using bisulfite sequencing (BS-Seq), which exploits the bisulfite-mediated deamination of cytosine to uracil for which the corresponding transformation of 5mC is much slower (16). However, it has been recognized that both 5mC and 5hmC are very slow to deaminate in the bisulfite reaction and so these two bases cannot be discriminated (17, 18). Two relatively new and elegant single molecule methods have shown promise in detecting 5mC and 5hmC at single nucleotide resolution. Single molecule real-time sequencing (SMRT) has been shown to detect derivatised 5hmC in genomic DNA (19). However, enrichment of DNA fragments containing 5hmC is required, which leads to loss of quantitative information (19). 5mC can be detected, albeit with lower accuracy, by SMRT (19). Furthermore, SMRT has a relatively high rate of sequencing errors (20), the peak calling of modifications is imprecise (19) and the platform has not yet sequenced a whole genome. Protein and solid-state nanopores can resolve 5mC from 5hmC and have the potential to sequence unamplified DNA molecules with further development (21, 22).

The present inventors have devised methods that allow modified cytosine residues, such as 5-methylcytosine (5mC), 5-hydroxymethylcytosine (5hmC) and 5-formylcytosine (5fC) to be distinguished from cytosine (C) at single nucleotide resolution. These methods are applicable to all sequencing platforms and may be useful, for example in the analysis of genomic DNA and/or of RNA.

An aspect of the invention provides a method of identifying a modified cytosine residue in a sample nucleotide sequence, comprising;

(i) providing a population of polynucleotides which comprise the sample nucleotide sequence, (ii) oxidising or reducing a first portion of said population, (iii) treating the oxidised or reduced first portion of said population and a second portion of said population with bisulfite, (iv) sequencing the polynucleotides in the first and second portions of the population following steps ii) and iii) to produce first and second nucleotide sequences, respectively, and;

(v) identifying residues in the first and second nucleotide sequences which correspond to a cytosine residue in the sample nucleotide sequence.

The residues identified in the first and second nucleotide sequences which correspond to a cytosine residue in the sample nucleotide sequence are indicative of the modification of the cytosine residue.

For example, cytosine residues may be present at one or more positions in the sample nucleic acid sequence. The residues at these one or more positions in the first and second nucleotide sequences may be identified. A modified cytosine at a position in the sample nucleotide sequence may be identified from combination of residues identified in the first and second nucleotide sequences respectively (i.e. C and C, U and U, C and U, or U and C) at that position. The cytosine modifications which are indicated by different combinations are shown in table 1.

A modified cytosine residue may contain a modification at the 5 position. Suitable modified cytosines include 5-substituted cytosines.

Groups which may be substituted at the 5-position of cytosine include methyl (m); hydroxymethyl (hm) or formyl (f) groups.

The methods described herein may be useful in identifying and/or distinguishing cytosine (C), 5-methylcytosine (5mC), 5-hydroxymethylcytosine (5hmC) and 5-formylcytosine (5fC) in a sample nucleotide sequence. For example, methods described herein may be useful in distinguishing one residue from the group consisting of cytosine (C), 5-methylcytosine (5mC), 5-hydroxymethylcytosine (5hmC) and 5-formylcytosine (5fC) from the other residues in the group.

Preferably, modified cytosine residues, such as 5-hydroxymethylcytosine, in the first portion of said population are not labelled, for example with substituent groups, such as glucose, before the oxidisation or reduction of step ii).

In some embodiments of the invention, the first portion of polynucleotides from the population may be oxidised. For example, 5-hydroxymethylcytosine residues in the first portion of polynucleotides may be converted into 5-formylcytosine (5fC) by oxidation and the first portion of polynucleotides then treated with bisulfite.

A method of identifying a modified cytosine residue in a sample nucleotide sequence may comprise;

(i) providing a population of polynucleotides which comprise the sample nucleotide sequence,
(ii) oxidising a first portion of said population,
(iii) treating the oxidised first portion of said population and a second portion of said population with bisulfite,
(iv) sequencing the polynucleotides in the first and second portions of the population following steps ii) and iii) to produce first and second nucleotide sequences, respectively and;
(v) identifying the residue in the first and second nucleotide sequences which corresponds to a cytosine residue in the sample nucleotide sequence.

The identification of a residue at a position in one or both of the first and second nucleotide sequences as cytosine in one or both of first and second nucleotide sequences is indicative that the cytosine residue in the sample nucleotide sequence is 5-methylcytosine or 5-hydroxymethylcytosine.

5-hydroxymethylcytosine (5hmC) may be identified in the sample nucleotide sequence. A uracil residue at a position in the first nucleotide sequence which corresponds to a cytosine in the sample nucleotide sequence and a cytosine at the same position in the second nucleotide sequence are indicative that the cytosine residue in the sample nucleotide sequence is 5-hydroxylmethylcytosine (5hmC).

For example, a method of identifying a 5-hydroxymethylcytosine (5hmC) residue in a sample nucleotide sequence or distinguishing 5-hydroxymethylcytosine from cytosine (C), 5-methylcytosine, and 5-formylcytosine (5fC) in a sample nucleotide sequence may comprise;
(i) providing a population of polynucleotides which comprise the sample nucleotide sequence,
(ii) oxidising a first portion of said population,
(iii) treating the oxidised first portion of said population and a second portion of said population with bisulfite,
(iv) sequencing the polynucleotides in the first and second portions of the population following steps ii) and iii) to produce first and second nucleotide sequences, respectively and;
(v) identifying the residue in the first and second nucleotide sequences which corresponds to a cytosine residue in the sample nucleotide sequence,
wherein the presence of a uracil residue in the first nucleotide sequence and a cytosine in the second nucleotide sequence is indicative that the cytosine residue in the sample nucleotide sequence is 5-hydroxylmethylcytosine.

5-methylcytosine (5mC) may be identified in a sample nucleotide sequence. Cytosine at a position in both the first and second nucleotide sequences that correspond to a cytosine residue in the sample nucleotide sequence are indicative that the cytosine residue in the sample nucleotide sequence is 5-methylcytosine (5mC).

For example, a method of identifying 5-methylcytosine in a sample nucleotide sequence or distinguishing 5-methylcytosine from cytosine (C), 5-hydroxymethylcytosine (5hmC) and 5-formylcytosine (5fC) in a sample nucleotide sequence may comprise;
(i) providing a population of polynucleotides which comprise the sample nucleotide sequence,
(ii) oxidising a first portion of said population,
(iii) treating the oxidised first portion of said population and a second portion of said population with bisulfite,
(iv) sequencing the polynucleotides in the first and second portions of the population following steps ii) and iii) to produce first and second nucleotide sequences, respectively and;
(v) identifying the residue in the first and second nucleotide sequences which corresponds to a cytosine residue in the sample nucleotide sequence
wherein the presence of a cytosine in both the first and second nucleotide sequences is indicative that the cytosine residue in the sample nucleotide sequence is 5-methylcytosine (5mC).

Uracil residues at a position in both the first and second nucleotide sequences which correspond to a cytosine in the sample nucleotide sequence are indicative that the cytosine residue in the sample nucleotide sequence is not 5-methylcytosine or 5-hydroxymethylcytosine i.e. the cytosine residue is unmodified cytosine or 5-formylcytosine.

A summary of the cytosine modifications at a position in the sample nucleotide sequence which are indicated by specific combinations of cytosine and uracil at the position in the first and second nucleotide sequences is shown in Table 1.

The first and second portions of the polynucleotide population may be treated with bisulfite and/or sequenced simultaneously or sequentially.

In some embodiments in which the first portion is oxidised in step ii), treatment of the second portion may not be required to identity or distinguish a modified cytosine residue in the sample nucleotide sequence. For example, Table 1 shows that oxidation and bisulfite treatment of the first portion of the polynucleotide population is sufficient to identify 5-methylcytosine in the sample nucleotide sequence. A method of identifying 5-methylcytosine in a sample nucleotide sequence or distinguishing 5-methylcytosine from cytosine (C), 5-hydroxymethylcytosine (5hmC) and 5-formylcytosine (5fC) in a sample nucleotide sequence may comprise;
(i) providing a population of polynucleotides which comprise the sample nucleotide sequence,
(ii) oxidising said population,
(iii) treating the oxidised population with bisulfite,
(iv) sequencing the polynucleotides in the population following steps ii) and iii) to produce a treated nucleotide sequence, and;
(v) identifying the residue in the treated nucleotide sequence which corresponds to a cytosine residue in the sample nucleotide sequence, wherein the presence of a cytosine in the treated nucleotide sequence is indicative that the cytosine residue in the sample nucleotide sequence is 5-methylcytosine (5mC).

In some embodiments of the invention, the first portion of polynucleotides from the population may be reduced in step ii). A method of identifying a modified cytosine residue in a sample nucleotide sequence may comprise;
(i) providing a population of polynucleotides which comprise the sample nucleotide sequence,
(ii) reducing a first portion of said population,
(iii) treating the reduced first portion of said population and a second portion of said population with bisulfite,
(iv) sequencing the polynucleotides in the first and second portions of the population following steps ii) and ii) to produce first and second nucleotide sequences, respectively and;
(v) identifying the residue in the first and second nucleotide sequences which corresponds to a cytosine residue in the sample nucleotide sequence.

This may be useful in identifying and/or distinguishing 5-formylcytosine (5fC) in a sample nucleotide sequence.

In embodiments in which the first portion is reduced, cytosine at a position in the first nucleotide sequence which corresponds to a cytosine in the sample nucleotide sequence and a uracil residue at this position in the second nucleotide sequence is indicative that the cytosine residue in the sample nucleotide sequence is 5-formylcytosine; uracil at a position in the first and second nucleotide sequences which corresponds to a cytosine residue in the sample nucleotide sequence is indicative that the cytosine residue in the sample nucleotide sequence is unmodified cytosine; and cytosine at a position in both the first and second nucleotide sequences which corresponds to a cytosine residue in the sample nucleotide sequence is indicative that the cytosine residue in the sample nucleotide sequence is 5-methylcytosine (5mC) or 5-hydroxymethylcytosine (5hmC).

A summary of the cytosine modifications at a position in the sample nucleotide sequence which are indicated by specific combinations of cytosine and uracil at the position in the first and second nucleotide sequences is shown in Table 1.

In some embodiments, methods of the invention may comprise sequencing a first portion of polynucleotides which has been oxidised and bisulfite treated; a second portion of polynucleotides which has been bisulfite treated; and a third portion of polynucleotides from the population which has been reduced and bisulfite treated. For example, a method may comprise;

(i) providing a population of polynucleotides which comprise the sample nucleotide sequence,
(ii) providing first, second and third portions of the population,
(iii) oxidising the first portion of said population,
(iv) reducing the third portion of said population,
(v) treating the first, second and third portions of said population with bisulfite,
(vi) sequencing the polynucleotides in the first, second and third portions of the population following steps iii), iv) and v) to produce first, second and third nucleotide sequences, respectively and;
(vii) identifying the residue in the first, second and third nucleotide sequences which corresponds to a cytosine residue in the sample nucleotide sequence.

This may be useful, for example, in identifying and/or distinguishing 5-formylcytosine (5fC) in a sample nucleotide sequence from cytosine and/or other modified cytosines.

Uracil at a position in the first and second nucleotide sequences which corresponds to a cytosine residue in the sample nucleotide sequence and a cytosine at this position in the third nucleotide sequence is indicative that the cytosine residue in the sample nucleotide sequence is 5-formylcytosine.

Cytosine at a position in the first, second and third nucleotide sequences which corresponds to a cytosine residue in the sample nucleotide sequence is indicative that the cytosine residue in the sample nucleotide sequence is 5-methylcytosine (5mC).

Cytosine at a position in the second and third nucleotide sequences which corresponds to a cytosine in the sample nucleotide sequence and a uracil residue at this position in the first nucleotide sequence is indicative that the cytosine residue in the sample nucleotide sequence is 5-hydroxymethylcytosine.

Uracil at a position in the first, second and third nucleotide sequences which corresponds to a cytosine residue in the sample nucleotide sequence is indicative that the cytosine residue in the sample nucleotide sequence is unmodified cytosine.

A summary of the cytosine modifications at a position in the sample nucleotide sequence which are indicated by specific combinations of cytosine and uracil at the position in the first, second and third nucleotide sequences is shown in Table 1.

The sample nucleotide sequence may be already known or it may be determined. The sample nucleotide sequence is the sequence of untreated polynucleotides in the population i.e. polynucleotides which have not been oxidised, reduced or bisulfite treated. In the sample nucleotide sequence, modified cytosines are not distinguished from cytosine. 5-Methylcytosine, 5-formylcytosine and 5-hydroxymethylcytosine are all indicated to be or identified as cytosine residues in the sample nucleotide sequence. For example, any of the methods described herein may further comprise;

providing a fourth portion of the population of polynucleotides comprising sample nucleotide sequence; and,
sequencing the polynucleotides in the fourth portion to produce the sample nucleotide sequence.

The sequence of the polynucleotides in the fourth portion may be determined by any appropriate sequencing technique.

The positions of one or more cytosine residues in the sample nucleotide sequence may be determined. This may be done by standard sequence analysis. Since modified cytosines are not distinguished from cytosine, cytosine residues in the sample nucleotide sequence may be cytosine, 5-methylcytosine, 5-formylcytosine or 5-hydroxymethylcytosine.

The first and second nucleotide sequences and, optionally the third nucleotide sequence, may be compared to the sample nucleotide sequence. For example, the residues at positions in the first and second sequences and, optionally the third nucleotide sequence, corresponding to the one or more cytosine residues in the sample nucleotide sequence may be identified.

The modification of a cytosine residue in the sample nucleotide sequence may be determined from the identity of the nucleotides at the corresponding positions in the first and second nucleotide sequences and, optionally the third nucleotide sequence.

The polynucleotides in the population all contain the same sample nucleotide sequence i.e. the sample nucleotide sequence is identical in all of the polynucleotides in the population.

The effect of different treatments on cytosine residues within the sample nucleotide sequence can then be determined, as described herein.

The sample nucleotide sequence may be a genomic sequence. For example, the sequence may comprise all or part of the sequence of a gene, including exons, introns or upstream or downstream regulatory elements, or the sequence may comprise genomic sequence that is not associated with a gene. In some embodiments, the sample nucleotide sequence may comprise one or more CpG islands.

Suitable polynucleotides include DNA, preferably genomic DNA, and/or RNA, such as genomic RNA (e.g. mammalian, plant or viral genomic RNA), mRNA, tRNA, rRNA and non-coding RNA.

The polynucleotides comprising the sample nucleotide sequence may be obtained or isolated from a sample of cells, for example, mammalian cells, preferably human cells.

Suitable samples include isolated cells and tissue samples, such as biopsies.

Modified cytosine residues including 5hmC and 5fC have been detected in a range of cell types including embryonic stem cells (ESCS) and neural cells (2, 3, 11, 37, 38).

Suitable cells include somatic and germ-line cells.

Suitable cells may be at any stage of development, including fully or partially differentiated cells or non-differentiated or pluripotent cells, including stem cells, such as adult or somatic stem cells, foetal stem cells or embryonic stem cells.

Suitable cells also include induced pluripotent stem cells (iPSCs), which may be derived from any type of somatic cell in accordance with standard techniques.

For example, polynucleotides comprising the sample nucleotide sequence may be obtained or isolated from neural cells, including neurons and glial cells, contractile muscle cells, smooth muscle cells, liver cells, hormone synthesising cells, sebaceous cells, pancreatic islet cells, adrenal cortex cells, fibroblasts, keratinocytes, endothelial and urothelial cells, osteocytes, and chondrocytes.

Suitable cells include disease-associated cells, for example cancer cells, such as carcinoma, sarcoma, lymphoma, blastoma or germ line tumour cells.

Suitable cells include cells with the genotype of a genetic disorder such as Huntington's disease, cystic fibrosis, sickle cell disease, phenylketonuria, Down syndrome or Marfan syndrome.

Methods of extracting and isolating genomic DNA and RNA from samples of cells are well-known in the art. For example, genomic DNA or RNA may be isolated using any convenient isolation technique, such as phenol/chloroform extraction and alcohol precipitation, caesium chloride density gradient centrifugation, solid-phase anion-exchange chromatography and silica gel-based techniques.

In some embodiments, whole genomic DNA and/or RNA isolated from cells may be used directly as a population of polynucleotides as described herein after isolation. In other embodiments, the isolated genomic DNA and/or RNA may be subjected to further preparation steps.

The genomic DNA and/or RNA may be fragmented, for example by sonication, shearing or endonuclease digestion, to produce genomic DNA fragments. A fraction of the genomic DNA and/or RNA may be used as described herein. Suitable fractions of genomic DNA and/or RNA may be based on size or other criteria. In some embodiments, a fraction of genomic DNA and/or RNA fragments which is enriched for CpG islands (CGIs) may be used as described herein.

The genomic DNA and/or RNA may be denatured, for example by heating or treatment with a denaturing agent. Suitable methods for the denaturation of genomic DNA and RNA are well known in the art.

In some embodiments, the genomic DNA and/or RNA may be adapted for sequencing before oxidation or reduction and bisulfite treatment, or bisulfite treatment alone. The nature of the adaptations depends on the sequencing method that is to be employed. For example, for some sequencing methods, primers may be ligated to the free ends of the genomic DNA and/or RNA fragments following fragmentation. Suitable primers may contain 5mC to prevent the primer sequences from altering during oxidation or reduction and bisulfite treatment, or bisulfite treatment alone, as described herein. In other embodiments, the genomic DNA and/or RNA may be adapted for sequencing after oxidation, reduction and/or bisulfite treatment, as described herein.

Following fractionation, denaturation, adaptation and/or other preparation steps, the genomic DNA and/or RNA may be purified by any convenient technique.

Following preparation, the population of polynucleotides may be provided in a suitable form for further treatment as described herein. For example, the population of polynucleotides may be in aqueous solution in the absence of buffers before treatment as described herein.

Polynucleotides for use as described herein may be single or double-stranded.

The population of polynucleotides may be divided into two, three, four or more separate portions, each of which contains polynucleotides comprising the sample nucleotide sequence. These portions may be independently treated and sequenced as described herein.

Preferably, the portions of polynucleotides are not treated to add labels or substituent groups, such as glucose, to 5-hydroxymethylcytosine residues in the sample nucleotide sequence before oxidation and/or reduction.

The first portion of the population of polynucleotides comprising the sample nucleotide sequence may be oxidised. Oxidation converts any 5-hydroxymethylcytosine in the sample nucleotide sequence to 5-formylcytosine. Oxidation may be non-enzyme mediated oxidation, for example using an organic or inorganic chemical oxidising agent, preferably under denaturing conditions.

The first portion may be oxidised by treatment with an oxidising agent. The oxidising agent is any agent suitable for generating an aldehyde from an alcohol. The oxidising agent or the conditions employed in the oxidation step may be selected so that any 5-hydroxymethylcytosine is selectively oxidised. Thus, substantially no other functionality in the polynucleotide is oxidised in the oxidation step. The oxidising step therefore does not result in the reaction of any thymine or 5-methylcytosine residues, where such are present. The agent or conditions are selected to minimise or prevent any degradation of the polynucleotide.

The use of an oxidising agent may result in the formation of some corresponding 5-carboxycytosine product. The formation of this product does not negatively impact on the methods of identification described herein. Under the bisulfite reaction conditions that are used to convert 5-formylcytosine to uracil, 5-carboxycytosine is observed to convert to uracil also. It is understood that a reference to 5-formylcytosine that is obtained by oxidation of 5-hydroxymethylcytosine may be a reference to a product also comprising 5-carboxycytosine that is also obtained by that oxidization.

The oxidising agent may be a non-enzymatic oxidising agent, for example, an organic or inorganic chemical compound.

Suitable oxidising agents are well known in the art and include metal oxides, such as $KRuO_4$, $MnO_2$ and $KMnO4$. Particularly useful oxidising agents are those that may be used in aqueous conditions, as such are most convenient for the handling of the polynucleotide. However, oxidising agents that are suitable for use in organic solvents may also be employed where practicable.

In some embodiments, the oxidising agent may comprise a perruthenate anion ($RuO_4^-$). Suitable perruthenate oxidising agents include organic and inorganic perruthenate salts, such as potassium perruthenate (KRuO4) and other metal perruthenates; tetraalkylammonium perruthenates, such as tetrapropylammonium perruthenate (TPAP) and tetrabutylammonium perruthenate (TBAP); polymer-supported perruthenate (PSP) and tetraphenylphosphonium ruthenate.

Advantageously, the oxidising agent or the oxidising conditions may also preserve the polynucleotide in a denatured state.

Following treatment with the oxidising agent, the polynucleotides in the first portion may be purified.

Purification may be performed using any convenient nucleic acid purification technique. Suitable nucleic acid purification techniques include spin-column chromatography.

The polynucleotide may be subjected to further, repeat oxidising steps. Such steps are undertaken to maximise the conversion of 5-hydroxycytosine to 5-formylcytosine. This may be necessary where a polynucleotide has sufficient secondary structure that is capable of re-annealing. Any annealed portions of the polynucleotide may limit or prevent access of the oxidising agent to that portion of the structure, which has the effect of protecting 5-hydroxycytosine from oxidation.

In some embodiments, the first portion of the population of polynucleotides may for example be subjected to multiple cycles of treatment with the oxidising agent followed by purification. For example, one, two, three or more than three cycles may be performed.

In some embodiments, the first portion of the population of polynucleotides comprising the sample nucleotide sequence may be reduced. In other embodiments, the third portion of the population of polynucleotides comprising the sample nucleotide sequence may be reduced. Reduction of the first or third portion of polynucleotides converts 5-formylcytosine residues in the sample nucleotide sequence into 5-hydroxymethylcytosine The first or third portions of polynucleotides may be reduced by treatment with a reducing agent. The reducing agent is any agent suitable for generating an alcohol from an aldehyde. The reducing agent or the conditions employed in the reduction step may be selected so that any 5-formylcytosine is selectively reduced (i.e. the reducing agent or reduction conditions are selective for 5-formylcytosine). Thus, substantially no other functionality in the polynucleotide is reduced in the reduction step. The reducing agent or conditions are selected to minimise or prevent any degradation of the polynucleotide.

Suitable reducing agents are well-known in the art and include $NaBH_4$, $NaCNBH_4$ and $LiBH_4$. Particularly useful reducing agents are those that may be used in aqueous conditions, as such are most convenient for the handling of the polynucleotide. However, reducing agents that are suitable for use in organic solvents may also be employed where practicable.

Following oxidation and reduction respectively, the first portion of the population, and optionally the third portion, are treated with bisulfite. A second portion of the population which has not been oxidised or reduced is also treated with bisulfite.

Bisulfite treatment converts both cytosine and 5-formylcytosine residues in a polynucleotide into uracil. As noted above, where any 5-carboxycytosine is present (as a product of the oxidation step), this 5-carboxycytosine is converted into uracil in the bisulfite treatment. Without wishing to be bound by theory, it is believed that the reaction of the 5-formylcytosine proceeds via loss of the formyl group to yield cytosine, followed by a subsequent deamination to give uracil. The 5-carboxycytosine is believed to yield the uracil through a sequence of decarboxylation and deamination steps. Bisulfite treatment may be performed under conditions that convert both cytosine and 5-formylcytosine or 5-carboxycytosine residues in a polynucleotide as described herein into uracil.

A portion of the population may be treated with bisulfite by incubation with bisulfite ions ($HSO_3^{2-}$).

The use of bisulfite ions ($HSO_3^{2-}$) to convert unmethylated cytosines in nucleic acids into uracil is standard in the art and suitable reagents and conditions are well known to the skilled person (39-42). Numerous suitable protocols and reagents are also commercially available (for example, EPITECT™, Qiagen NL; EZ DNA METHYLATION™, Zymo Research Corp CA; CPGENOME™ Turbo Bisulfite Modification Kit; Millipore).

A feature of the methods described herein is the conversion of unmethylated cytosine (which may be generated in situ from 5-formylcytosine or 5-carboxycytosine) to uracil. This reaction is typically achieved through the use of bisulfite. However, in general aspects of the invention, any reagent or reaction conditions may be used to effect the conversion of cytosine to uracil. Such reagents and conditions are selected such that little or no 5-methylcytosine reacts, and more specifically such that little or no 5-methylcytosine reacts to form uracil. The reagent, or optionally a further reagent, may also effect the conversion of 5-formylcytosine or 5-carboxycytosine to cytosine or uracil.

Following the incubation, the portions of polynucleotides may be immobilised, washed, desulfonated, eluted and/or otherwise treated as required.

In some embodiments, the first, second and third portions of polynucleotides from the population may be amplified following treatment as described above. This may facilitate further manipulation and/or sequencing. Sequence alterations in the first, second and third portions of polynucleotides are preserved following the amplification. Suitable polynucleotide amplification techniques are well known in the art and include PCR. The presence of a uracil (U) residue at a position in the first, second and/or third portions of polynucleotide may be indicated or identified by the presence of a thymine (T) residue at that position in the corresponding amplified polynucleotide.

As described above, polynucleotides may be adapted after oxidation, reduction and/or bisulfite treatment to be compatible with a sequencing technique or platform. The nature of the adaptation will depend on the sequencing technique or platform. For example, for Solexa-Illumina sequencing, the treated polynucleotides may be fragmented, for example by sonication or restriction endonuclease treatment, the free ends of the polynucleotides repaired as required, and primers ligated onto the ends.

Polynucleotides may be sequenced using any convenient low or high throughput sequencing technique or platform, including Sanger sequencing (43), Solexa-Illumina sequencing (44), Ligation-based sequencing (SOLID™) (45), pyrosequencing (46); strobe sequencing (SMRT™) (47, 48); and semiconductor array sequencing (ION TORRENT™) (49).

Suitable protocols, reagents and apparatus for polynucleotide sequencing are well known in the art and are available commercially.

The residues at positions in the first, second and/or third nucleotide sequences which correspond to cytosine in the sample nucleotide sequence may be identified.

The modification of a cytosine residue at a position in the sample nucleotide sequence may be determined from the identity of the residues at the corresponding positions in the first, second and, optionally, third nucleotide sequences, as described above.

The extent or amount of cytosine modification in the sample nucleotide sequence may be determined. For example, the proportion or amount of 5-hydroxymethylcytosine and/or 5-methylcytosine in the sample nucleotide sequence compared to unmodified cytosine may be determined.

Polynucleotides as described herein, for example the population of polynucleotides or 1, 2, 3, or all 4 of the first, second, third and fourth portions of the population, may be immobilised on a solid support.

A solid support is an insoluble, non-gelatinous body which presents a surface on which the polynucleotides can be immobilised. Examples of suitable supports include glass slides, microwells, membranes, or microbeads. The support may be in particulate or solid form, including for example a plate, a test tube, bead, a ball, filter, fabric, polymer or a membrane. Polynucleotides may, for example, be fixed to an inert polymer, a 96-well plate, other device, apparatus or material which is used in a nucleic acid sequencing or other investigative context. The immobilisation of polynucleotides to the surface of solid supports is well-known in the art. In some embodiments, the solid support itself may be immobilised. For example, microbeads may be immobilised on a second solid surface.

In some embodiments, the first, second, third and/or fourth portions of the population of polynucleotides may be amplified before sequencing. Preferably, the portions of polynucleotide are amplified following the treatment with bisulfite.

Suitable methods for the amplification of polynucleotides are well known in the art.

Following amplification, the amplified portions of the population of polynucleotides may be sequenced.

Nucleotide sequences may be compared and the residues at positions in the first, second and/or third nucleotide sequences which correspond to cytosine in the sample nucleotide sequence may be identified, using computer-based sequence analysis.

Nucleotide sequences, such as CpG islands, with cytosine modification greater than a threshold value may be identified. For example, one or more nucleotide sequences in which greater than 1%, greater than 2%, greater than 3%, greater than 4% or greater than 5% of cytosines are hydroxymethylated may be identified.

Computer-based sequence analysis may be performed using any convenient computer system and software. A typical computer system comprises a central processing unit (CPU), input means, output means and data storage means (such as RAM). A monitor or other image display is preferably provided. The computer system may be operably linked to a DNA and/or RNA sequencer.

For example, a computer system may comprise a processor adapted to identify modified cytosines in a sample nucleotide sequence by comparison with first, second and/or third nucleotide sequences as described herein. For example the processor may be adapted;
(a) identify the positions of cytosine residues in the sample nucleotide sequence,
(b) identify the residues in the first, second and/or third nucleotide sequences at the positions of cytosine residues in the sample nucleotide sequence,
(c) determine from the identities of said residues the presence or absence of modification of the cytosine residue at the positions in the sample nucleotide sequence.

The sample nucleotide sequence and the first second and third nucleotide sequences may be entered into the processor automatically from the DNA and/or RNA sequencer. The sequences may be displayed, for example on a monitor.

The computer system may further comprise a memory device for storing data. Nucleotide sequences such as genomic sequences, and the positions of 5fC, 5hmC and other modified cytosine residues may be stored on another or the same memory device, and/or may be sent to an output device or displayed on a monitor. This may facilitate the mapping of modified cytosines, such as 5hmC and 5fC, in genomic DNA.

The identification and mapping of cytosine modifications, such as 5fC and 5hmC, in the genome may be useful in the study of neural development and function, and cell differentiation, division and proliferation, as well as the prognosis and diagnosis of diseases, such as cancer.

The identification and/or mapping of modified cytosines such as 5fC and 5hmC, using the methods described herein may therefore be useful in disease Another aspect of the invention provides a kit for use in a method of identifying a modified cytosine residue in a sample nucleotide sequence as described above, comprising;
a oxidising agent and/or a reducing agent; and,
a bisulfite reagent.

Suitable oxidising agents, reducing agents and bisulfite reagents are described above.

A kit may further comprise a population of control polynucleotides comprising one or more modified cytosine residues, for example cytosine (C), 5-methylcytosine (5mC), 5-hydroxymethylcytosine (5hmC) or 5-formylcytosine (5fC). In some embodiments, the population of control polynucleotides may be divided into one or more portions, each portion comprising a different modified cytosine residue.

The kit may include instructions for use in a method of identifying a modified cytosine residue as described above.

A kit may include one or more other reagents required for the method, such as buffer solutions, sequencing and other reagents. A kit for use in identifying modified cytosines may include one or more articles and/or reagents for performance of the method, such as means for providing the test sample itself, including DNA and/or RNA isolation and purification reagents, and sample handling containers (such components generally being sterile).

Various further aspects and embodiments of the present invention will be apparent to those skilled in the art in view of the present disclosure.

All documents mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments that are described.

Certain aspects and embodiments of the invention will now be illustrated by way of example and with reference to the figures described below.

FIG. 1 shows the method for single-base resolution sequencing of 5hmC. FIG. 1A shows the reaction of 2'-deoxy-5-formylcytidine (d5fC) with $NaHSO_3$ (bisulfite) quenched by NaOH at different time points then analyzed by high performance liquid chromatography (HPLC). Error bars are the standard deviation of 3 replicates. FIG. 1B shows the oxidative bisulfite reaction scheme: oxidation of 5hmC to 5fC followed by bisulfite treatment and NaOH to convert 5fC to U. The R group is DNA. FIG. 1C shows a diagram and table outlining the BS-Seq and oxBS-Seq techniques. BS-Seq consists of bisulfite treatment of the input DNA and then amplification followed by sequencing. oxBS-Seq consists of oxidation of the input DNA, followed by bisulfite treatment and amplification then sequencing. By comparing the input, BS-Seq and oxBS-Seq outputs C, 5mC and 5hmC can be discriminated, mapped and quantified.

FIG. 2A shows the bisulfite profiles of 2'deoxy-5-formylcytosine indicating an overall decarbonylation plus deamination to uracil. FIG. 2B shows the bisulfite profile of 2'deoxy-5-carboxycytosine indicating a decarboxylation to cytosine then a deamination to uracil.

FIG. 3 shows quantification of oxidation by mass spectrometry (FIGS. 3A, 3B, 3D) and oxidative bisulfite treatment by Illumina sequencing (FIG. 3C). FIG. 3A shows levels of 5hmC and 5fC (peak areas normalised to T) in a 15mer ssDNA oligonucleotide before and after $KRuO_4$ oxidation. FIG. 3B shows levels of 5hmC and 5fC (concentration normalised to 5mC in primer sequence) in a 135mer dsDNA fragment before and after two sequential $KRuO_4$ oxidations. FIG. 3C shows C to T conversion levels as determined by Illumina sequencing of two dsDNA fragments containing either a single 5hmCpG (122mer) or multiple 5hmCpGs (135 mer) following oxidative bisulfite treatment (at least 950,000 reads were obtained per base). 5mC was also present in these strands for comparison of conversion rates. FIG. 3D shows levels of 5hmC and 5fC (concentration normalised to 5mC in primer sequence) in ES cell DNA (J1) measured before and after KRuO$_4$ oxidation. All error bars are standard deviations.

FIG. 4 shows the extent of cytosine degradation after oxidation as determined by measuring the change of nucleoside ratios following oxidation with KRuO$_4$ on synthetic 15mer single stranded (ss) DNA containing C (three replicates) (FIG. 4A), synthetic 15mer ssDNA containing 5mC (three replicates) (FIG. 4B) and genomic ES cell J1 DNA (2 replicates of sonicated and 2 of non-sonicated) (FIG. 4C). Percent change measured by HPLC analysis of nucleoside peak area after oxidation divided by nucleoside peak area before oxidation. Error bars are standard deviations.

Figure 8:
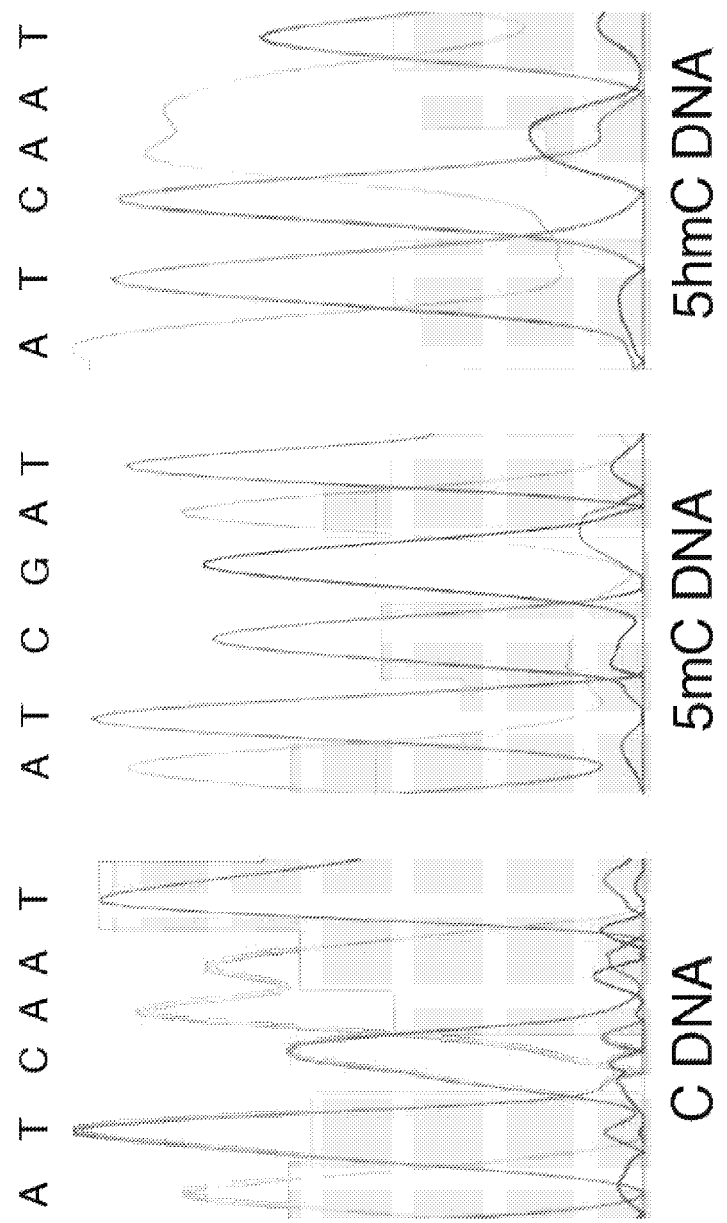

FIG. 8 shows Sanger sequencing of the 122mer DNA strand with a ClaI site (ATCGAT) containing either C, 5mC or 5hmC after oxBS treatment. The chromatogram shows the opposite sequence to the template strand. In the C DNA the C in the opposite strand is fully converted to a U, shown as an A in the chromatogram instead of a G. The 5mC DNA is not converted, showing a G in the chromatogram. The 5hmC DNA is mostly converted, showing an A in the chromatogram, with a small trace of unconverted G in this run.

Figure 9C:
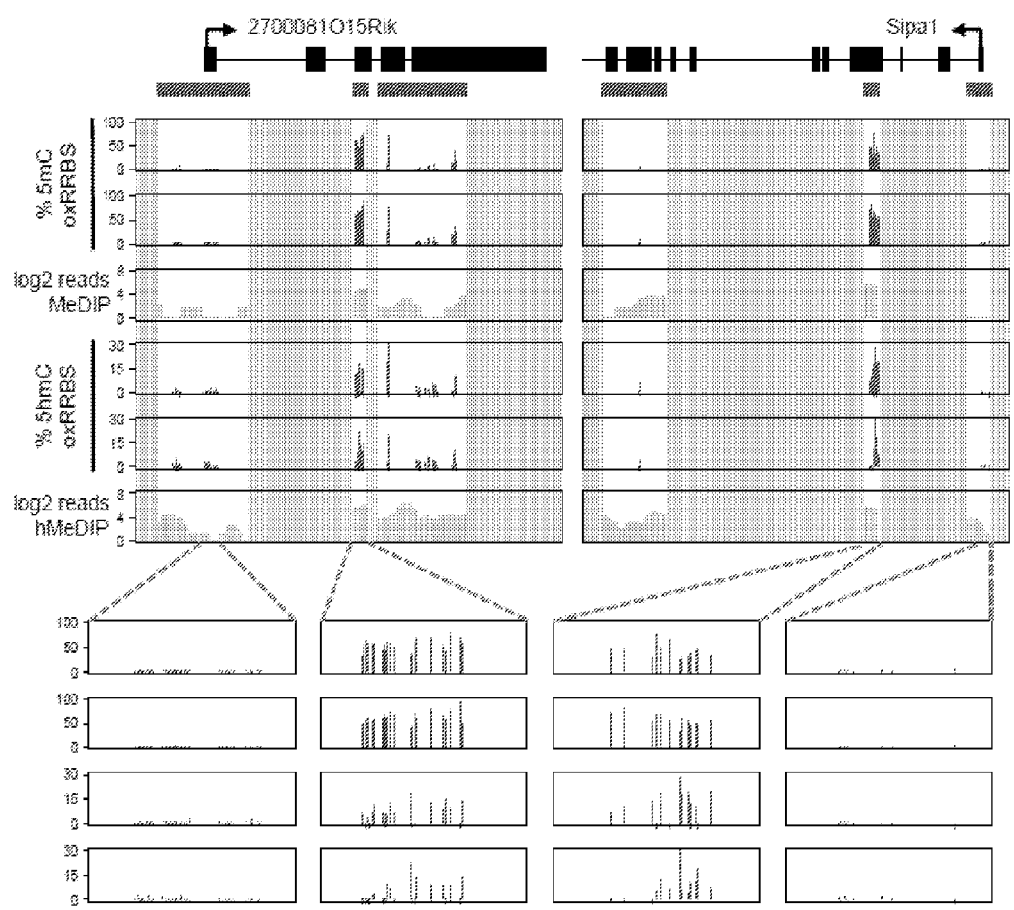
Figure 9D:
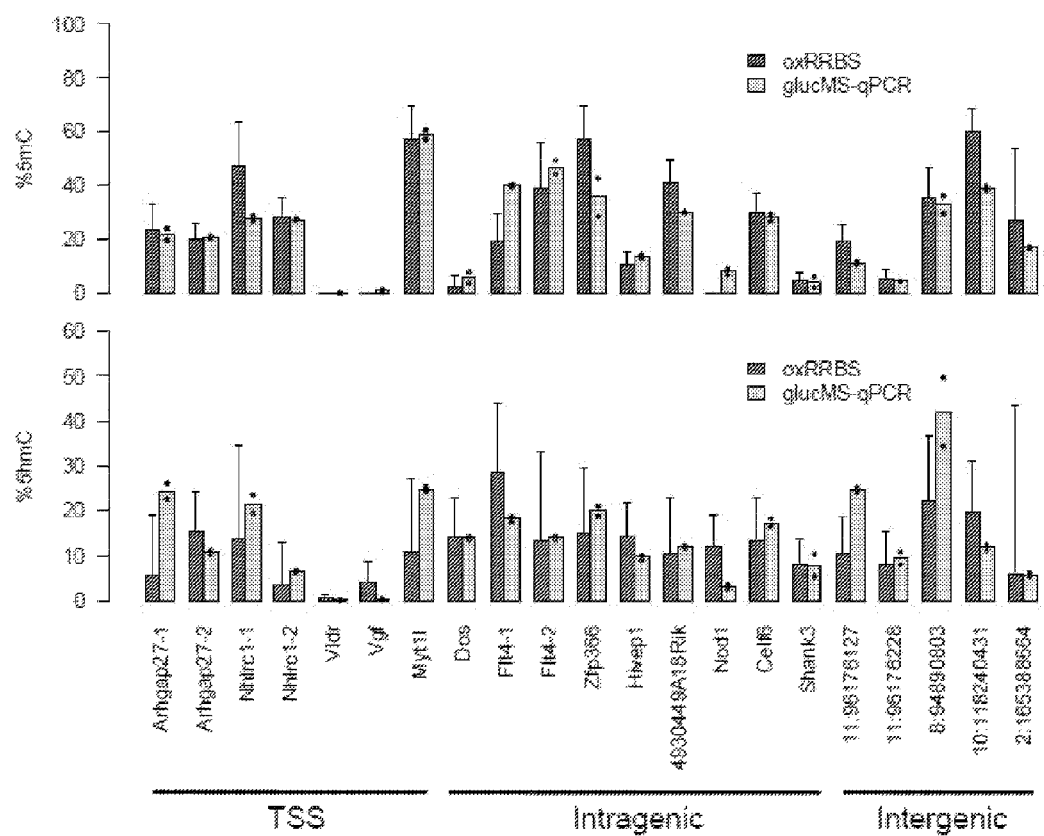

FIG. 9 shows quantification of 5mC and 5hmC levels at CGIs by oxRRBS. FIG. 9A shows that a comparison of the fraction of unconverted cytosines per CGI between the RRBS and oxRRBS datasets; CGIs with statistically significant lower fractions in the oxRRBS dataset (red) are hydroxymethylated CGIs; a false discovery rate of 3.7% was estimated using the number of CGIs with the opposite pattern (black). FIG. 9B shows the distribution of 5mC and 5hmC levels within CGIs with significant levels of the respective modification. FIG. 9C shows examples of genomic RRBS and oxRRBS profiles overlapped with (h)MeDIP-Seq profiles (6). CGIs are indicated by the green bars; for the purposes of clarity data outside CGIs was masked (grey areas). Each bar in the oxRRBS tracks represents a single CpG (in either DNA strand). Zoomed in areas in the lower part of the panel highlight the single nucleotide resolution of the method. FIG. 9D shows 5mC and 5hmC levels at selected CGIs were validated using glucMS-qPCR. Values from oxRRBS at individual MspI sites are displayed, with error bars representing 95% confidence intervals. GlucMS-qPCR was performed in duplicate, with the bar representing the mean value and the black dots the individual replicates. The two techniques show a good correlation.

Figure 10A:
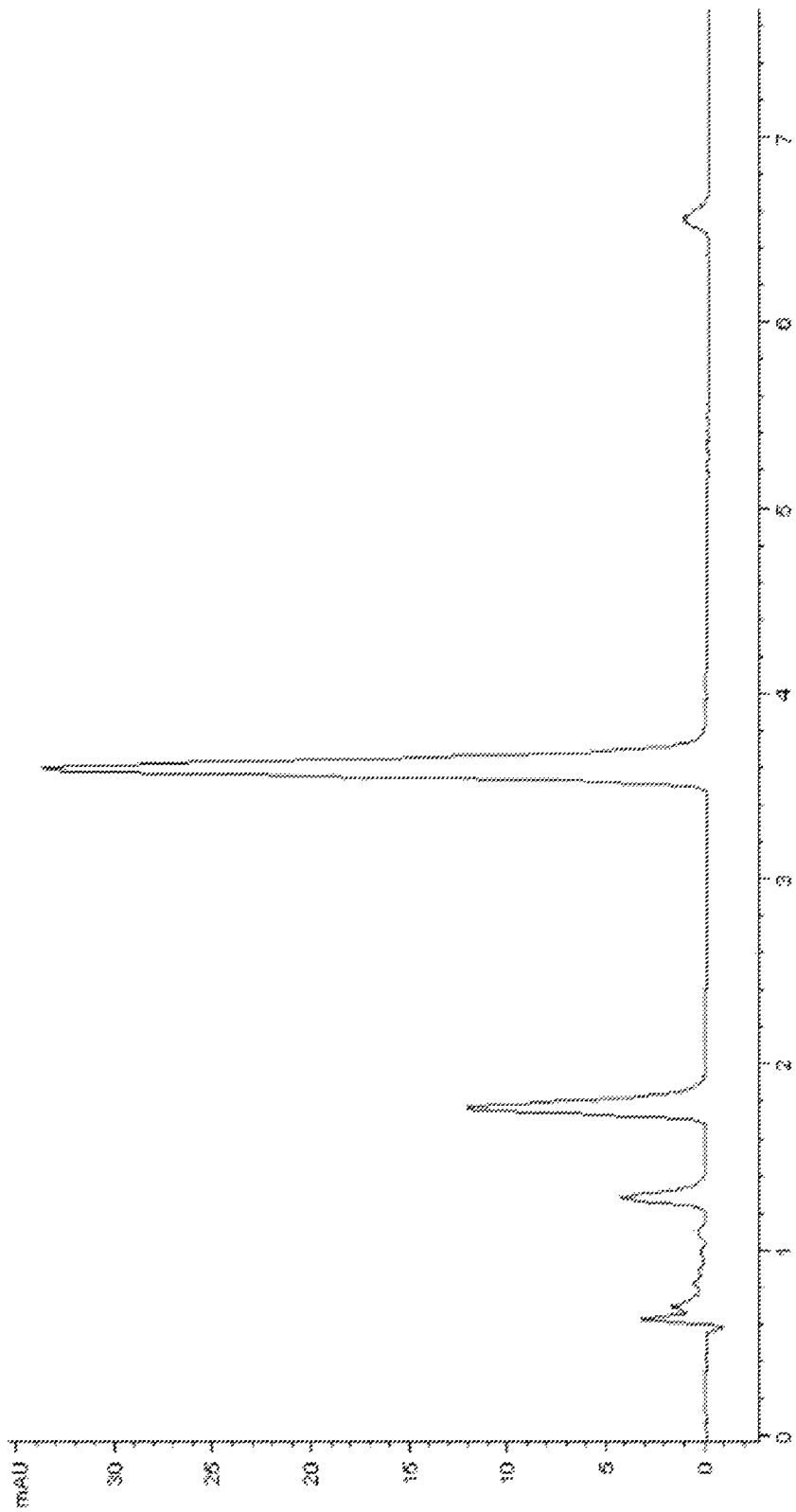

FIG. 10 shows an HPLC chromatogram of a RNA strand (SEQ ID NO: 7) digested to nucleosides before (FIG. 10A) and after (FIG. 10B) oxidation with KRuO$_4$. The same conditions were used as for DNA oxidation. The retention times of the nucleosides were as follows: C—1.2 min, U—1.7 min, G—3.5 min, A—6.5 min.

Figure 11:
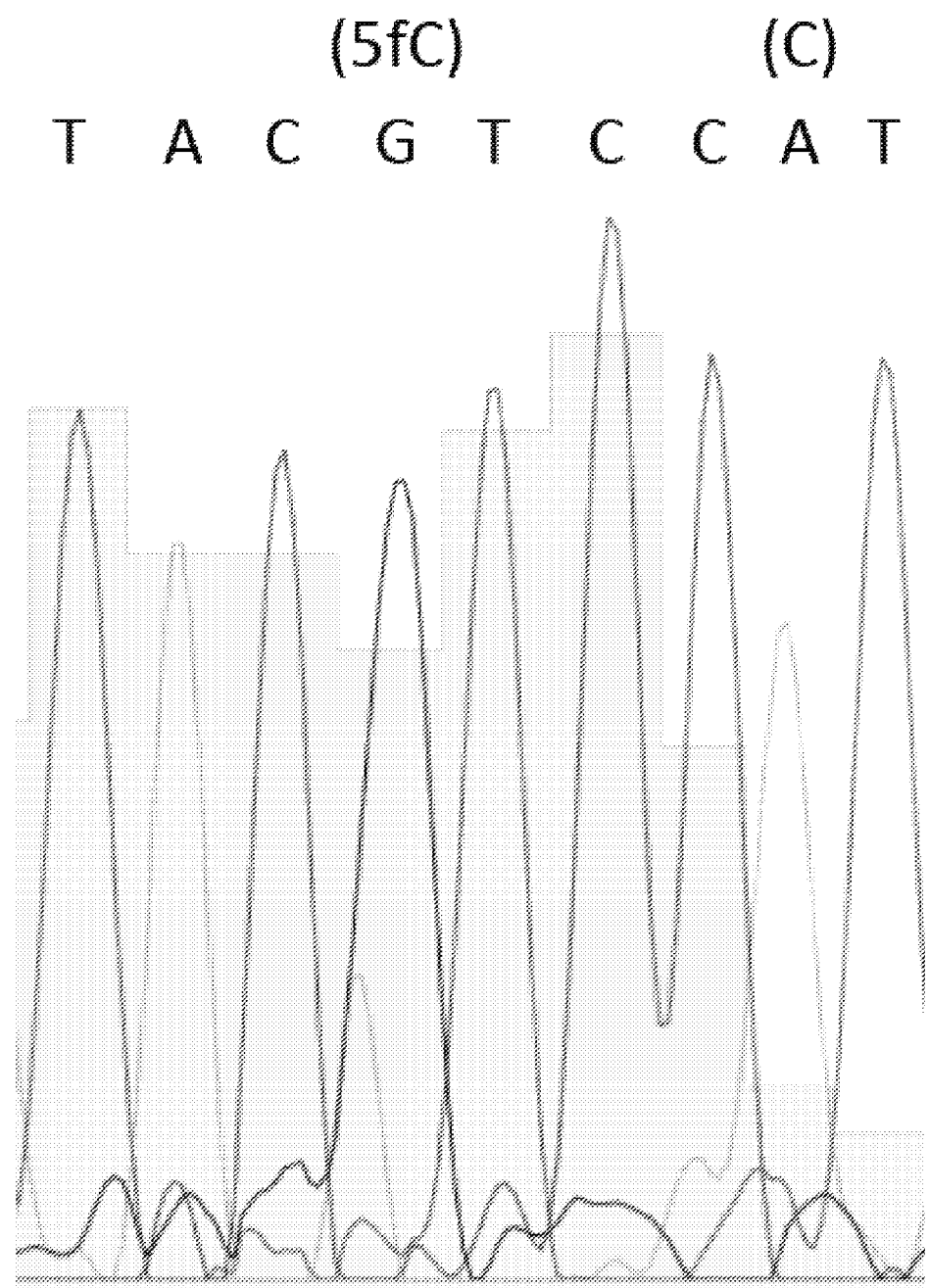

FIG. 11 shows a Sanger sequencing trace for a synthetic 100mer DNA strand containing a 5-formylcytosine (5fC) (partial sequence shown—ACGGA5fCGTA) following reduction with NaBH4 and bisulfite treatment (redBS-Seq). The chromatogram shows the reverse complement of the partial sequence (TACGTCCAT—where the bold positions come from 5fC or C). The positions of the 5fC and C (in brackets) are shown on the template strand in FIG. 11. Both 5fC and C deaminate under bisulfite conditions. However, 5fC is converted to 5hmC by the reduction step and not deaminated whereas deamination of C is unaffected. This allows the discrimination of 5fC and C at single-base resolution.

Table 1 shows sequencing outcomes for cytosine and modified cytosines subjected to various treatments.

Table 2 shows the structures of cytosine (1a), 5-methylcytosine (5mC; 1b), 5-hydroxymethylcytosine (5hmC; 1c) and 5-formylcytosine (5fC; 1d)

Table 3 shows a summary of the efficiencies of oxidation of 5hmC in DNA for some examples of water-soluble oxidants.

Figure 4:
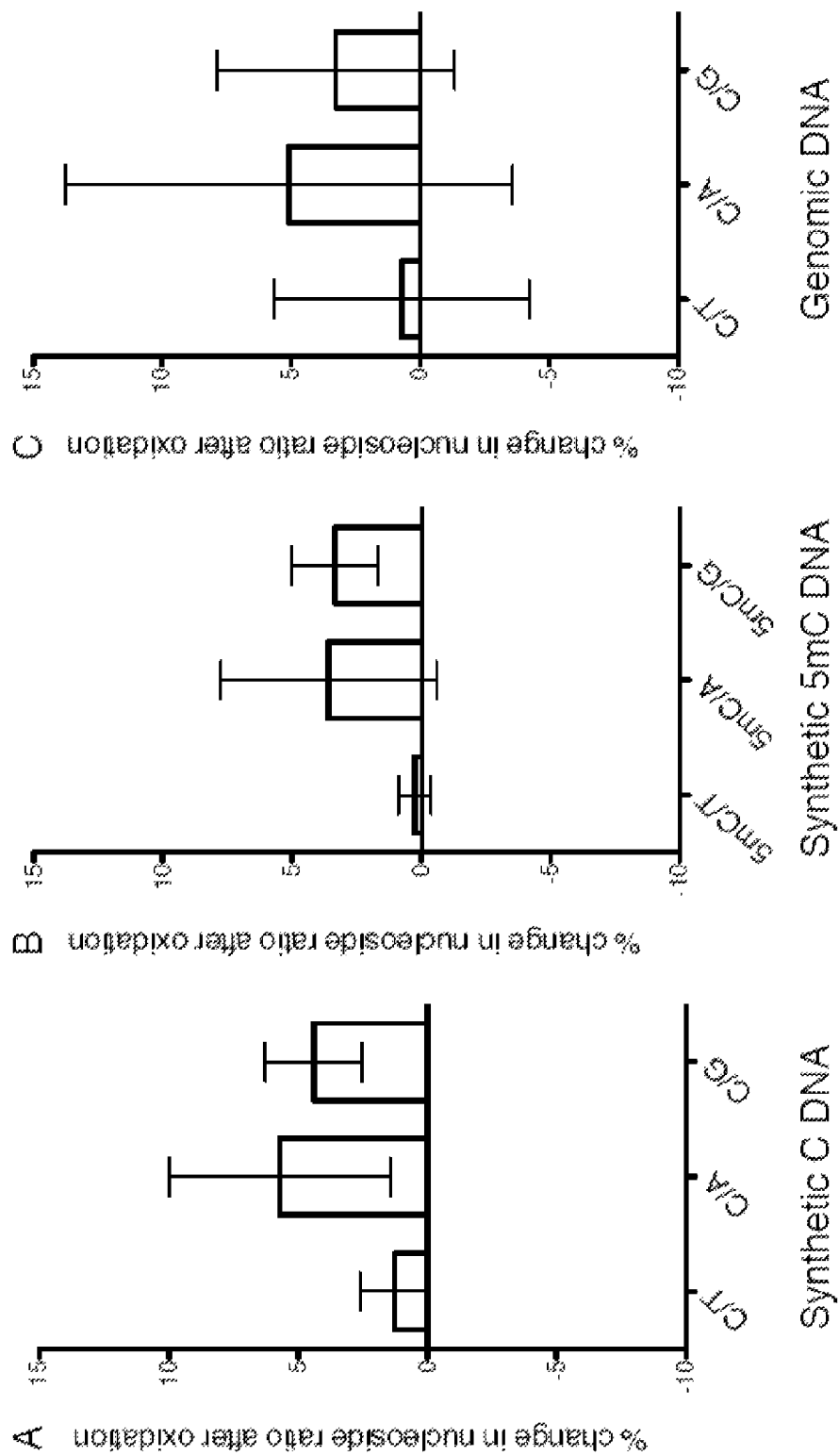
Figure 5A:
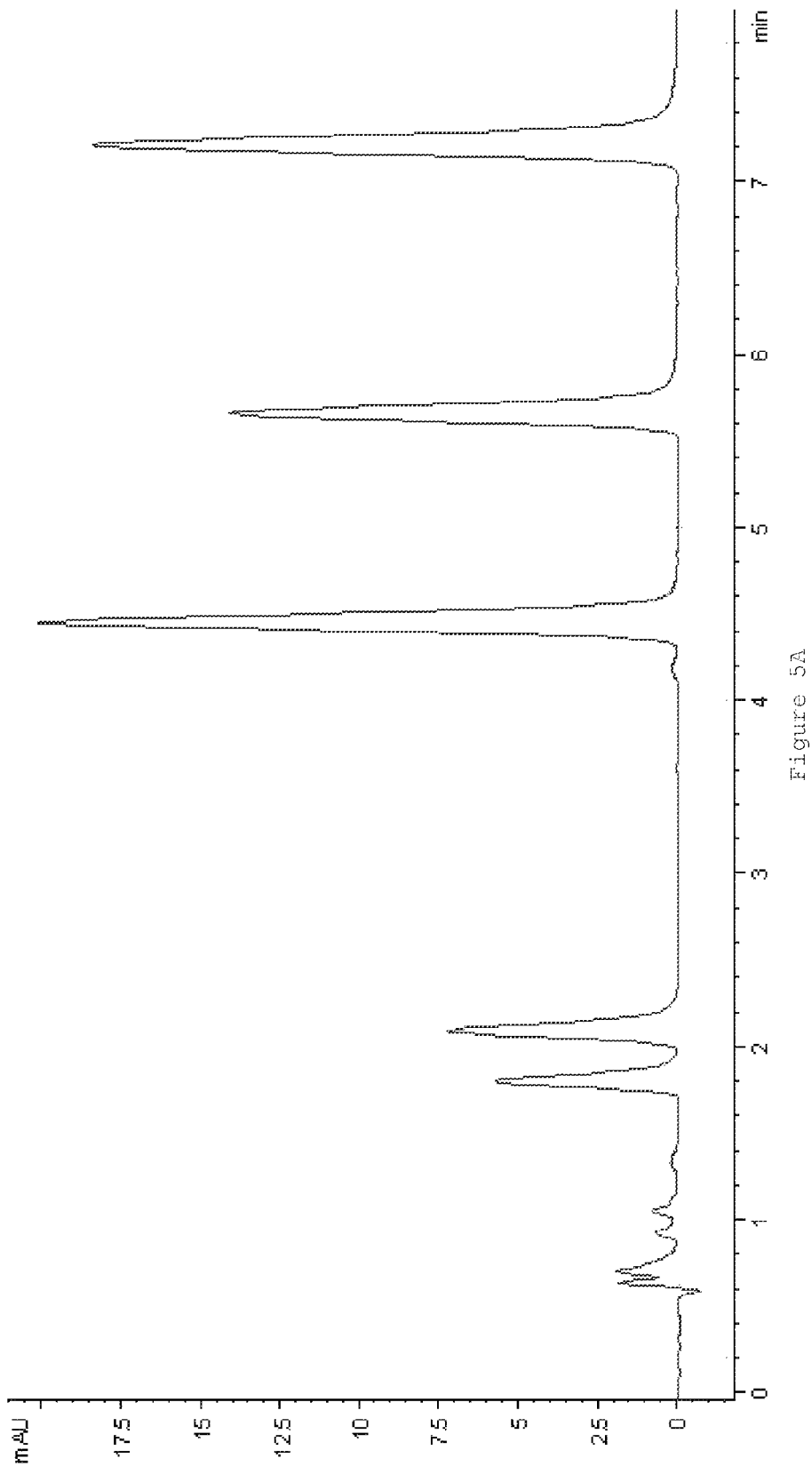
FIG. 5 shows an HPLC trace of the nucleosides obtained by digestion of a 140 bp DNA molecule containing 5hmC before (FIG. 5A) and after (FIG. 5B) oxidation.
Figure 5B:
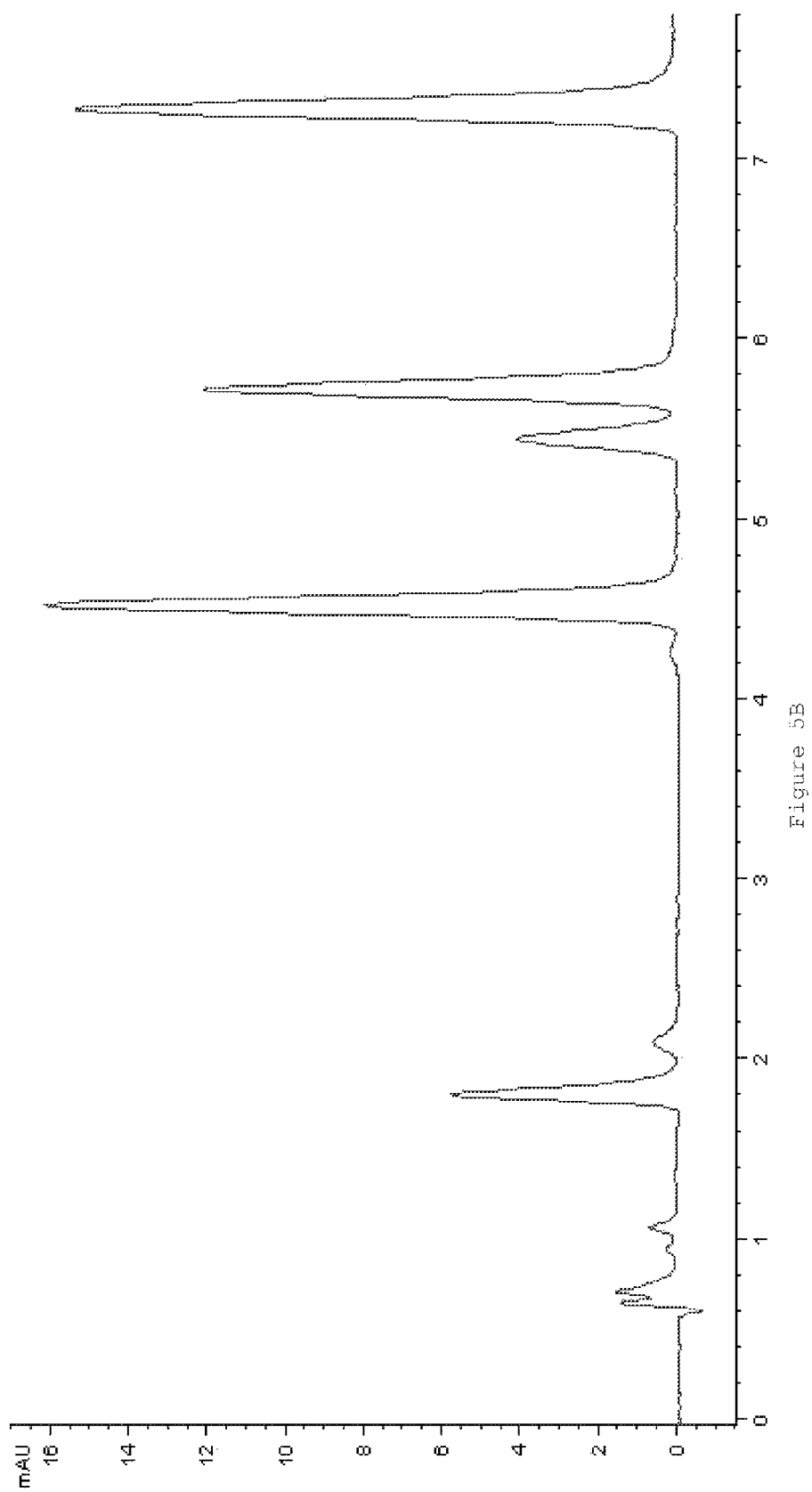

Tables 4 and 5 show the retention times for the peaks in the HLPC traces of DNA (FIGS. 4, 5 and 6) and RNA (FIG. 10) respectively.

EXPERIMENTS

1. Methods 1.1 d5hmCTP Oxidation to d5fCTP and d5cCTP with MnO$_2$ 2.5 μL d5hmCTP (100 mM, Bioline) in 497.5 μL H$_2$O with 51.6 mg MnO$_2$ (for d5fCTP) or 500 mg MnO$_2$ (for d5cCTP) (Alpha Aeser) was shaken at 50 degrees for 2 h and 30 min. Then MnO$_2$ was removed by filtration using Amicon Ultra 0.5 mL 10 kDa columns (Millipore) and the sample was lyophilized. The nucleotide triphosphate was resuspended (5 mM) and dephosphorylated with alkaline phosphatase (New England Biolabs) overnight at 37° C.

1.2 Bisulfite Timecourse with d5fC and d5cC Nucleoside

9 μL d5fC or d5cC (5 mM), 0.5 μL dA (0.1 M, Roche) and 2.5 μL H$_2$O were mixed and then 33 μL 4 M NaHSO$_3$ (MP Biochemicals) was added. This was split into three 15 uL reactions and held at 50° C. in the dark. 0.5 μL fractions were taken out at various time points and worked up in 2.5 μL H$_2$O and 2 μL NaOH (1 M). After being held for at least 30 min at room temperature they were injected into the HPLC. Peak areas were measured, correlated to a calibration curve of d5fC, d5cC, dC or dU, and standardised to the level of dA in the chromatogram.

1.3 DNA Digestion for HPLC Analysis

DNA was digested as by a literature protocol (30), purified with Amicon Ultra 0.5 mL 10 kDa columns and analysed by HPLC using an Agilent 1100 HPLC with a flow of 1 mL/min over an Eclipse XDB-C18 3.5 μm, 3.0×150 mm column. The column temperature was maintained at 45 degrees. Eluting buffers were buffer A (500 mM Ammonium Acetate (Fisher) pH 5), Buffer B (Acetonitrile) and Buffer C(H$_2$O). Buffer A was held at 1% throughout the whole run and the gradient for the remaining buffers was 0 min—0.5% B, 2 min—1% B, 8 min—4% B, 10 min—95% B.

The retention times of 2'-deoxynucleosides are as follows: 2'-deoxy-5-carboxycytidine (1.0 min), 2'-deoxycytidine (1.8 min), 2'-deoxy-5-hydroxymethylcytidine (2.1 min), 2'-deoxyuridine (2.7 min), 2'-deoxy-5-methylcytidine (4.0 min), 2'-deoxyguanosine (4.5 min), 2'-deoxy-5-formylcytidine (5.4 min), 2'-deoxythymidine (5.7 min), 2'-deoxyadeosine (7.4 min).

The same protocol was used to digest RNA for HPLC analysis.

1.4 Single and Double Stranded DNA Sequences

15mer oligos were purchased from IBA containing either cytosine, 5-methylcytosine, or 5-hydroxymethylcytosine. 122mer and 135mer dsDNA template and primers were purchased from Biomers. All C's in primers are 5-methylcytosine. 5-hydroxymethylcytosine was added to the strand at all other cytosine positions by PCR, using d5hmCTP and Fermentas DreamTaq Polymerase.

1.5 General Reduction

DNA (approx 1 µg-10 µL) was incubated on ice for 5 minutes with 40 µL of $NaBH_4$ (10,000 equivalents per µL). This reaction was then shaken at 25 degrees with an open lid in the dark for 1 hour. The reaction was purified with quick spin oligo columns (Roche).

1.6 Oxidations

General Oxidation

DNA was made up to 24 µL with NaOH (0.05 M final concentration) on ice, then 1 µL of a $KRuO_4$ (Alpha Aeser) solution (15 mM in 0.05 M NaOH) was added and the reaction was held on ice for 1 hour, with occasional vortexing. The reaction was purified with a mini quick spin oligo column (Roche) (after four 600 µL $H_2O$ washes).

These conditions were also used for the oxidation of RNA.

Single Stranded DNA Oxidation

1 µg 15mer synthetic ssDNA oxidised according to the general oxidation.

Synthetic Double Stranded DNA Double Oxidation

The dsDNA was precipitated with ethanol and then filtered through a mini quick spin oligo column (after four 600 uL $H_2O$ washes). A double oxidation was required for synthetic dsDNA as NaOH denaturation is not 100% efficient with a solution of a single homologous DNA fragment (unlike genomic DNA).

1 µg DNA was denatured in 0.05 M NaOH (total volume 19 µL) for 30 min at 37° C. The reaction was then snap cooled on ice and left for 5 min. The reaction was then oxidised according to the general oxidation but with a total volume of 20 µL. This DNA was re-denatured in 0.05 M NaOH (total volume 24 µL) for 30 min at 37° C. The reaction was again snap cooled on ice and left for 5 min and oxidised according to the general oxidation.

General Oxidation for Genomic DNA

DNA (1 µg or less) was precipitated with ethanol prior to oxidation then filtered through a mini quick spin oligo column (after four 600 µL $H_2O$ washes). DNA was denatured in 0.05 M NaOH (24 µL or 40 µL total volume) for 30 min at 37° C. This was then snap cooled on ice and left for 5 min and oxidised according to the general oxidation.

1.7 Sanger and Illumina Sequencing of Oxidative Bisulfite Treated dsDNA

For Sanger sequencing, 1 µg of 122mer DNA containing C, 5mC and 5hmC was oxidised according to the dsDNA double oxidation and bisulfite-treated using the Qiagen Epitect kit, according to the manufacturer's instructions for FFPE samples, except that the thermal cycle was run twice over. These samples were then submitted for Sanger sequencing (Source BioScience).

For Illumina sequencing, 1 µg of 122mer and 135mer DNA containing 5hmC was digested overnight with DraI (2 µL, New England Biolabs) and SspI (1 µL, New England Biolabs). The digested bands were gel purified with the Fermentas GeneJET gel extraction kit and methylated adaptors (Illumina) were ligated using the NEBNext DNA sample prep master mix set 1. After oxidation and bisulfite treatment as above, ligated fragments were amplified (18 cycles) using Pfu Turbo Cx (Agilent) and adaptor-specific primers (Illumina), followed by purification using AMPure XP beads (Agencourt).

1.8 Mass Spectrometry

Nucleosides were derived from DNA by digestion with DNA Degradase Plus (Zymo Research) according to the manufacturer's instructions and were analysed by LC-MS/MS on a LTQ Orbitrap Velos mass spectrometer (Thermo Scientific) fitted with a nanoelectrospray ion-source (Proxeon). Mass spectral data for 5hmC, 5fC, and where relevant 5mC and T, were acquired in high resolution full scan mode (R>40,000 for the protonated pseudomolecular ions and >50,000 for the accompanying protonated base fragment ions), and also in selected reaction monitoring (SRM) mode, monitoring the transitions 258→142.0611 (5hmC), 256→140.0455 (5fC), 242→126.0662 (5mC) and 243→127.0502 (T). Parent ions were selected for SRM with a 4 mass unit isolation window and fragmented by HCD with a relative collision energy of 20%, with R>14,000 for the fragment ions.

Peak areas from extracted ion chromatograms of the relevant ions for 5hmC and 5fC were normalised to those from either 5mC (where present) or T, and quantified by external calibration relative to standards obtained by digestion of nucleotide triphosphates or oligonucleotides.

1.9 ES Cell Culture and DNA Extraction

J1 ES cells (129S4/SvJae) were purchased from ATCC (Cat. SCRC-1010) and cultured on a γ-irradiated pMEF feeder layer at 37° C. and 5% $CO_2$ in complete ES medium (DMEM 4500 mg/L glucose, 4 mM L-glutamine and 110 mg/L sodium pyruvate, 15% fetal bovine serum, 100 U of penicillin/100 µg of streptomycin in 100 mL medium, 0.1 mM non-essential amino acids, 50 µM β-mercaptoethanol, 103U LIF ESGRO®). Genomic DNA was prepared from ES cells at passage 14 or 20 using the Qiagen Allprep DNA/RNA mini kit.

1.10 oxRRBS

RRBS libraries from oxidised and non-oxidised DNA were prepared based on a previously published protocol (31). Briefly, 2 µg of genomic DNA were digested with MspI (Fermentas) followed by end repair and A-tailing with Klenow (Fermentas) and ligation of methylated adaptors (Illumina) with T4 DNA ligase (NEB). Adaptor-ligated MspI-digested DNA was run on a 3% agarose gel and size selected (110-380 bp), followed by purification with the Qiagen QIAquick gel purification quick and ethanol precipitation.

Prior to oxidation, size-selected DNA was filtered through a mini quick spin oligo column (after four 600 µL $H_2O$ washes) to remove any last remaining buffers/salts and adjusted to a final volume of 25 µL. 5 µL of this solution were kept for generation of the non-oxidised library. The remaining was oxidised according to the general oxidation for genomic DNA.

Both oxidised and non-oxidised DNA samples were bisulfite-treated using the Qiagen Epitect kit, according to the manufacturer's instructions for FFPE samples, except that the thermal cycle was run twice over. Final library amplification (18 cycles) was done using Pfu Turbo Cx (Agilent) and adaptor-specific primers (Illumina), after which the libraries were purified using AMPure XP beads (Agencourt).

1.11 Sequencing and Read Alignment

Sequencing (single-end, 40 bp reads) was performed on the Illumina GAIIx platform. Bases were called by reprocessing raw images using OLB version 1.8 after applying bareback-processing to the first three base pairs (32). Bisulfite read alignments to the mouse genome (build NCBIM37) were carried out using Bismark v0.6.4 (33), using options -n 1 -l 40-phred64-quals-vanilla. Bismark alignments to individual LINE1 5' monomer sequences were performed slightly more stringently (-n 0); published consensus sequences were used for alignment of reads to L1A (34), L1Tf and L1Gf (35) monomer subtypes.

Bisulfite conversion rates were estimated from the number of unconverted cytosines at Klenow-filled in 3' MspI sites of sequencing reads that were short enough to read through these sites. Read phred quality remained high at 3' ends. Estimated bisulfite conversion rates varied between 99.8% and 99.9%.

1.12 oxRRBS Data Processing

The numbers of converted and unconverted cytosines within CGIs (25) were extracted from each BS and oxBS dataset. For each CpG position, the amount of 5mC was taken as the percentage of unconverted cytosines in each oxBS dataset, and the amount of 5hmC was taken by subtracting this value from the percentage of unconverted cytosines in the corresponding BS dataset. An overall value per CGI was calculated by pooling data from all the CpGs covered within each CGI. CpGs with fewer than 10 reads were excluded, as were CpGs for which the 5mC estimation deviated from the overall CGI 5mC value by more than 20% or the 5hmC estimation deviated from the overall value by more than 10%. After this outlier filtration step, only CGIs with 5 representative CpGs or more were analyzed.

To test for CGIs that contained 5mC levels significantly above the bisulfite conversion error of the oxBS dataset, a binomial test was applied using a Benjamini-Hochberg corrected p-value cutoff of 0.01. Similarly, a binomial test was used to select CGIs with significant amounts of unconverted cytosines in the BS dataset; within these, differences between the BS and oxBS datasets were tested by applying a Fisher's test and using a corrected p-value cutoff of 0.05. CGIs with a significantly lower fraction of unconverted cytosines in the oxBS dataset were taken as hydroxymethylated CGIs. CGIs with the opposite pattern are assumed to be artefacts and were used to estimate a false discovery rate.

1.13 GlucMS-qPCR

Quantification of 5mC and 5hmC levels at MspI sites by glucMS-qPCR was performed as previously described (6).

2. Results

Figure 1A:
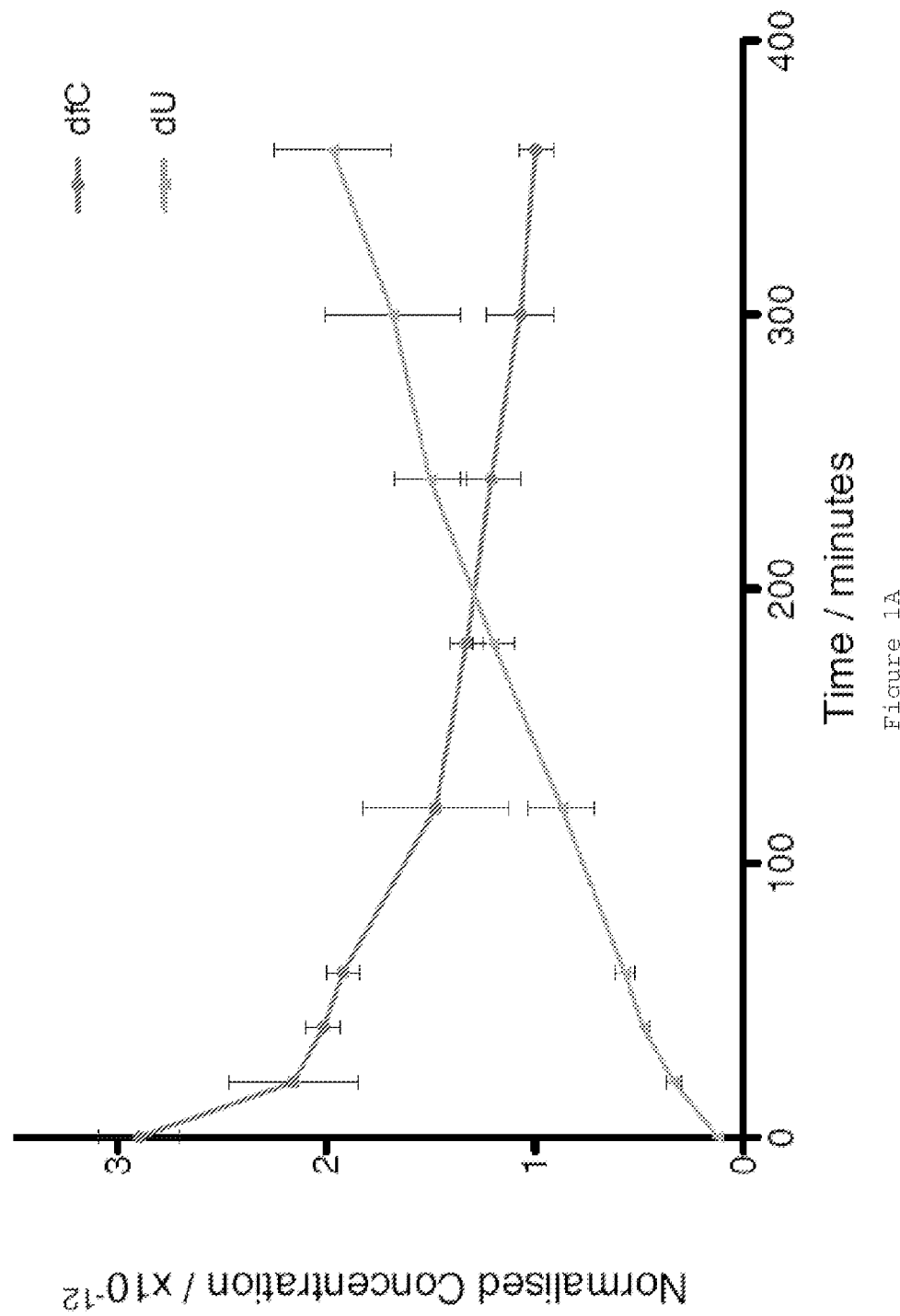
Figure 1B:
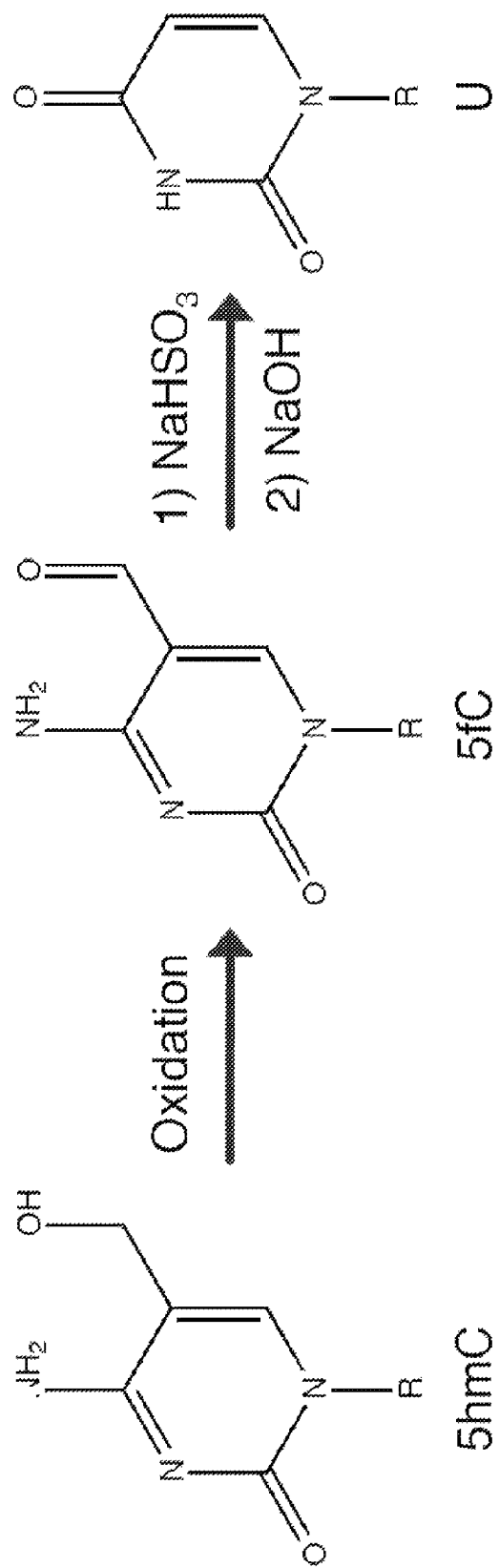
Figure 1C:
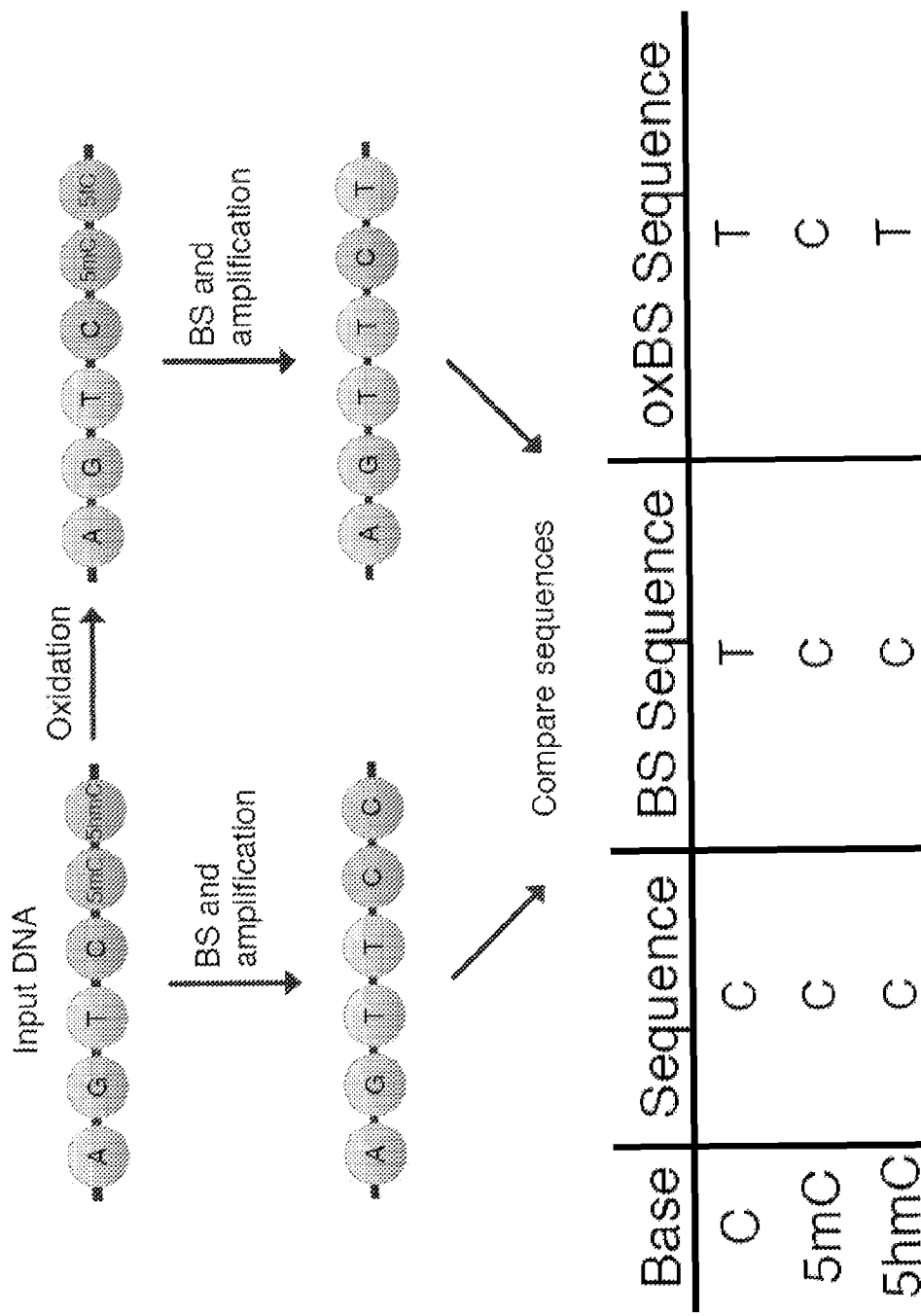

We pursued a strategy that would discriminate 5mC from 5hmC in DNA by exploiting chemical reactivity that is selective for 5hmC, in particular, by chemically removing the hydroxymethyl group and thus transforming 5hmC to C, which could then be readily transformed to U by bisulfite-mediated deamination. During our chemical reactivity studies on 5-formylcytosine (5fC), we observed the decarbonylation and deamination of 5fC to uracil (U) under bisulfite conditions that would leave 5mC unchanged (FIG. 1A). This previously unreported transformation indicated that 5hmC sequencing could be performed by selectively oxidising 5hmC to 5fC and then converting 5fC to U in a two-step procedure (FIG. 1B). Whilst conventional BS-Seq leads to both 5mC and 5hmC being detected as Cs, this 'oxidative bisulfite' sequencing (oxBS-Seq) approach yielded Cs only at 5mC sites and therefore allowed us to determine the amount of 5hmC at a particular nucleotide position by comparison of the readouts from BS-Seq and oxBS-Seq (FIG. 1C).

Figure 2A:
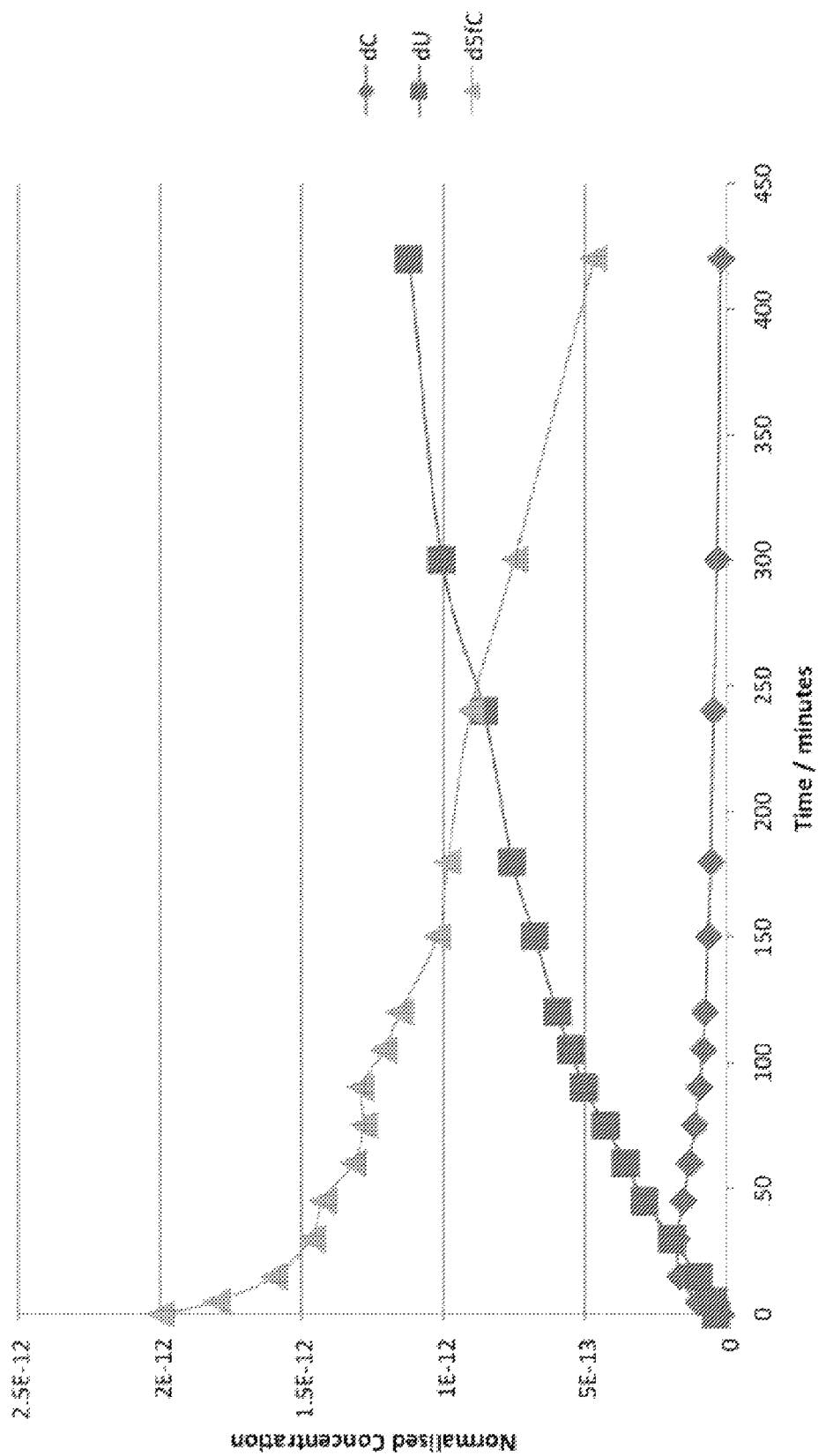
Figure 2B:
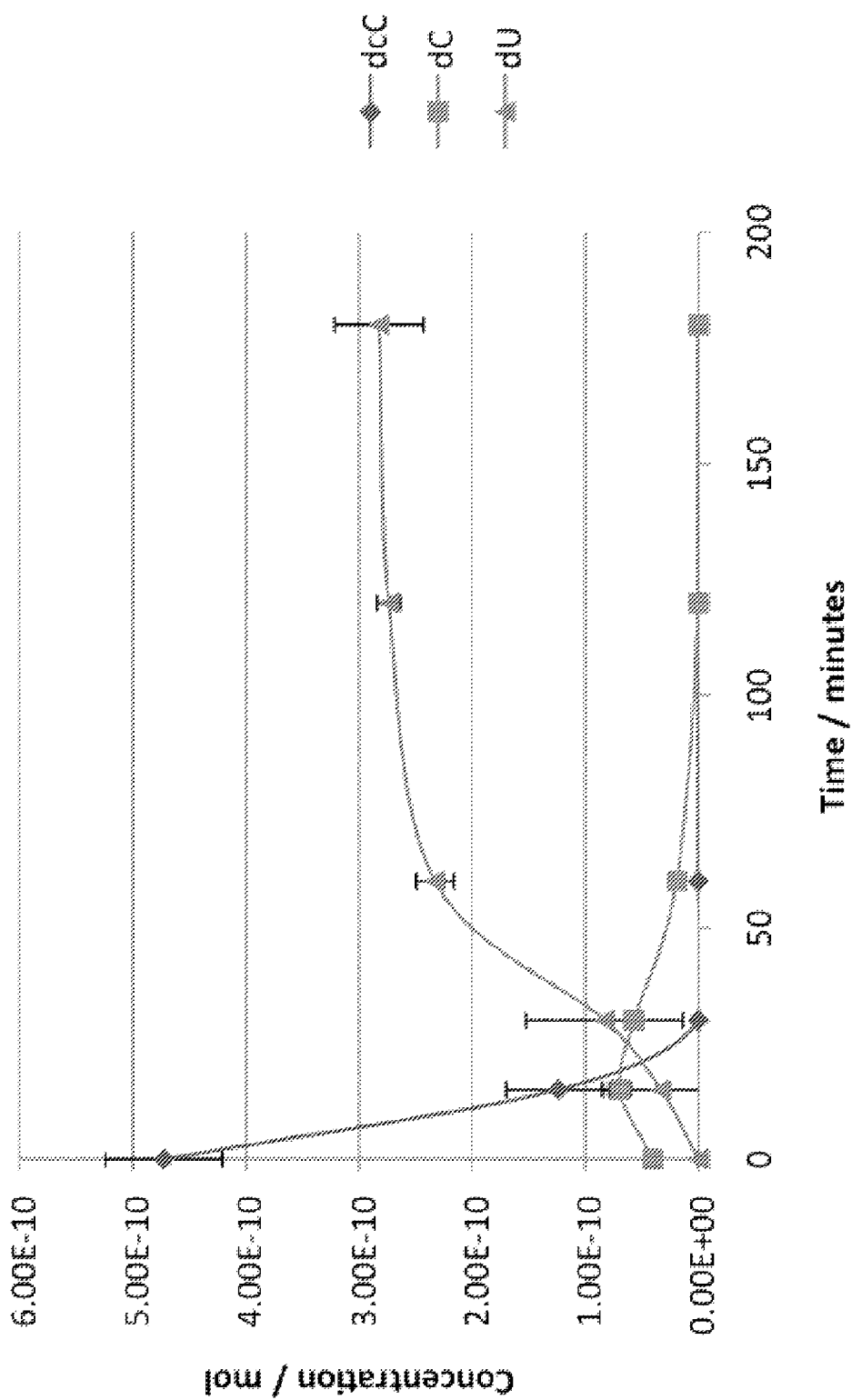

Bisulfite profiles of 2'deoxy-5-formylcytosine and 2'deoxy-5-carboxycytosine were determined (FIGS. 2A and 2B). 2'deoxy-5-formylcytosine and 2'deoxy-5-carboxycytosine were incubated with 2.9 M NaHSO4. Small samples of the reaction were taken at different time points and worked up in 0.3 M NaOH. These were injected directly into a HPLC for analysis. The HPLC profiles are consistent with overall decarbonylation or decarboxylation, respectively, to cytosine followed by a fast deamination to uracil.

Figure 3:
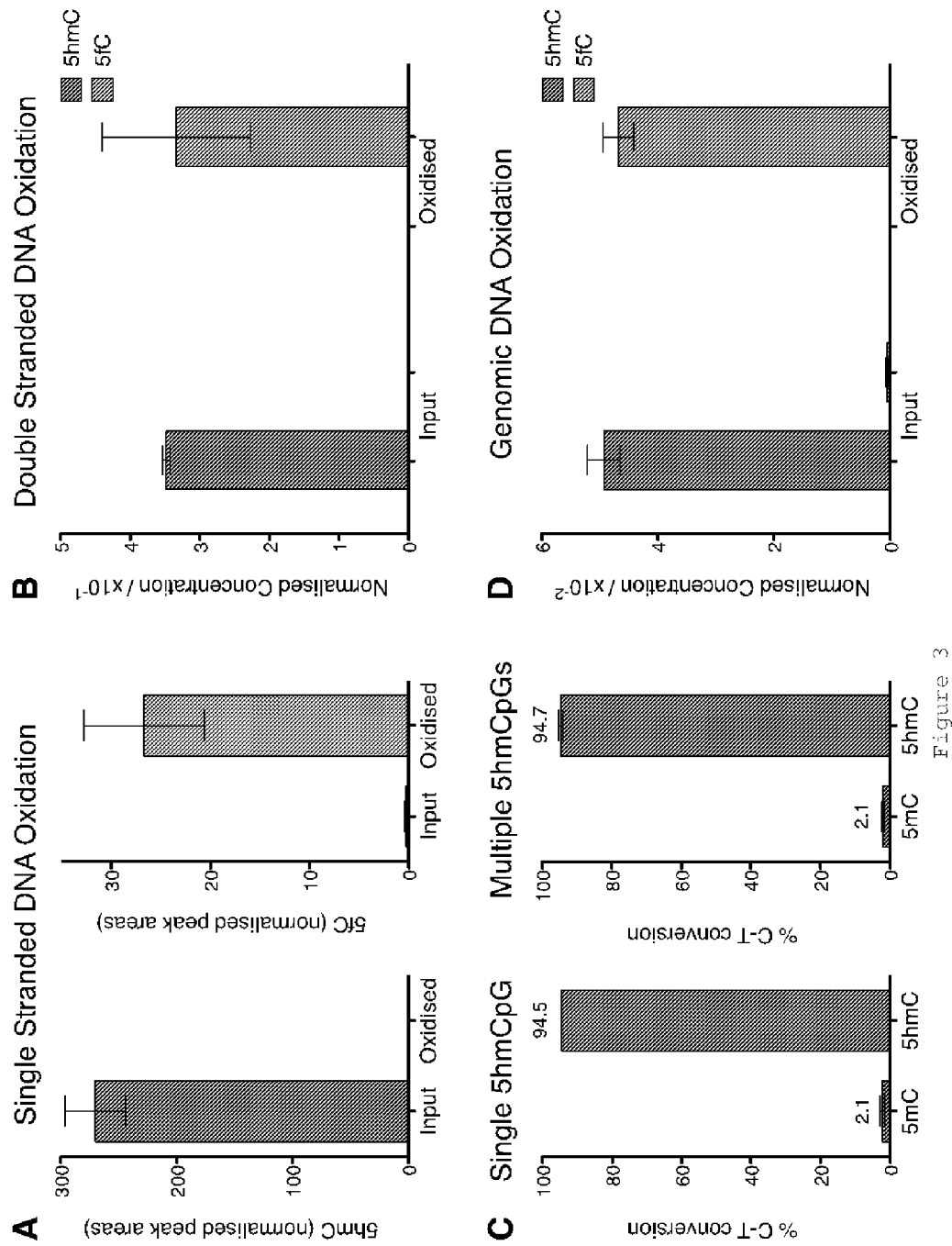

Therefore, we required specific oxidation of 5hmC to 5fC using an oxidant that was mild, compatible with aqueous media and selective over other bases and the DNA backbone. A range of potentially suitable water-soluble oxidants were tested (Table 3) and we found potassium perruthenate ($KRuO_4$) to possess the properties and conversion efficiency we sought. $KRuO_4$ can, in principle, oxidize both alcohols and carbon-carbon double bonds (23). However, in our reactivity studies on a synthetic 15mer single stranded DNA (ss-DNA) containing 5hmC, we established conditions under which $KRuO_4$ reactivity was highly specific for the primary alcohol of 5hmC (quantitative conversion of 5hmC to 5fC by mass spectrometry, FIG. 3A). 15mer ssDNA that contained C or 5mC, rather than 5hmC, did not show any base-specific reactions with $KRuO_4$ (FIGS. 4A, B). We were also aware that $KRuO_4$ oxidations could proceed to the carboxylic acid (23), however in the context of 5hmC in DNA, we only observed the aldehyde (5fC), even with a moderate excess of oxidant. The $KRuO_4$ oxidation is also capable of oxidizing 5hmC in samples presented as double stranded DNA (ds-DNA), with an initial denaturing step before the addition of the oxidant; this results in a quantitative yield of 5hmC to 5fC, as judged by mass spectrometry (FIG. 3B).

A 140 bp DNA molecule (SEQ ID NO: 1) was prepared which contained 45 5hmC nucleosides incorporated through PCR using 5-methylcytosine primers and hmCTP. The DNA was oxidised using KRuO4. Before and after oxidation, the DNA was digested to nucleosides with Benzonase, Phosphodiesterase I and Alkaline Phosphatase. This mixture was then injected into the HPLC, to give the traces shown in FIGS. 5A (before oxidation) and 5B (after oxidation). Almost complete conversion of 5hmC to 5fC was observed with no activity on other nucleosides.

A single stranded 15 bp DNA molecule (SEQ ID NO: 2) containing 3 5fC residues was treated with bisulfite as described above. Before and after bisulfite treatment, the DNA was digested to nucleosides with Benzonase, Phosphodiesterase I and Alkaline Phosphatase. This mixture was then injected into the HPLC, to give the traces shown in FIGS. 6A and 6B.

Figure 6B:
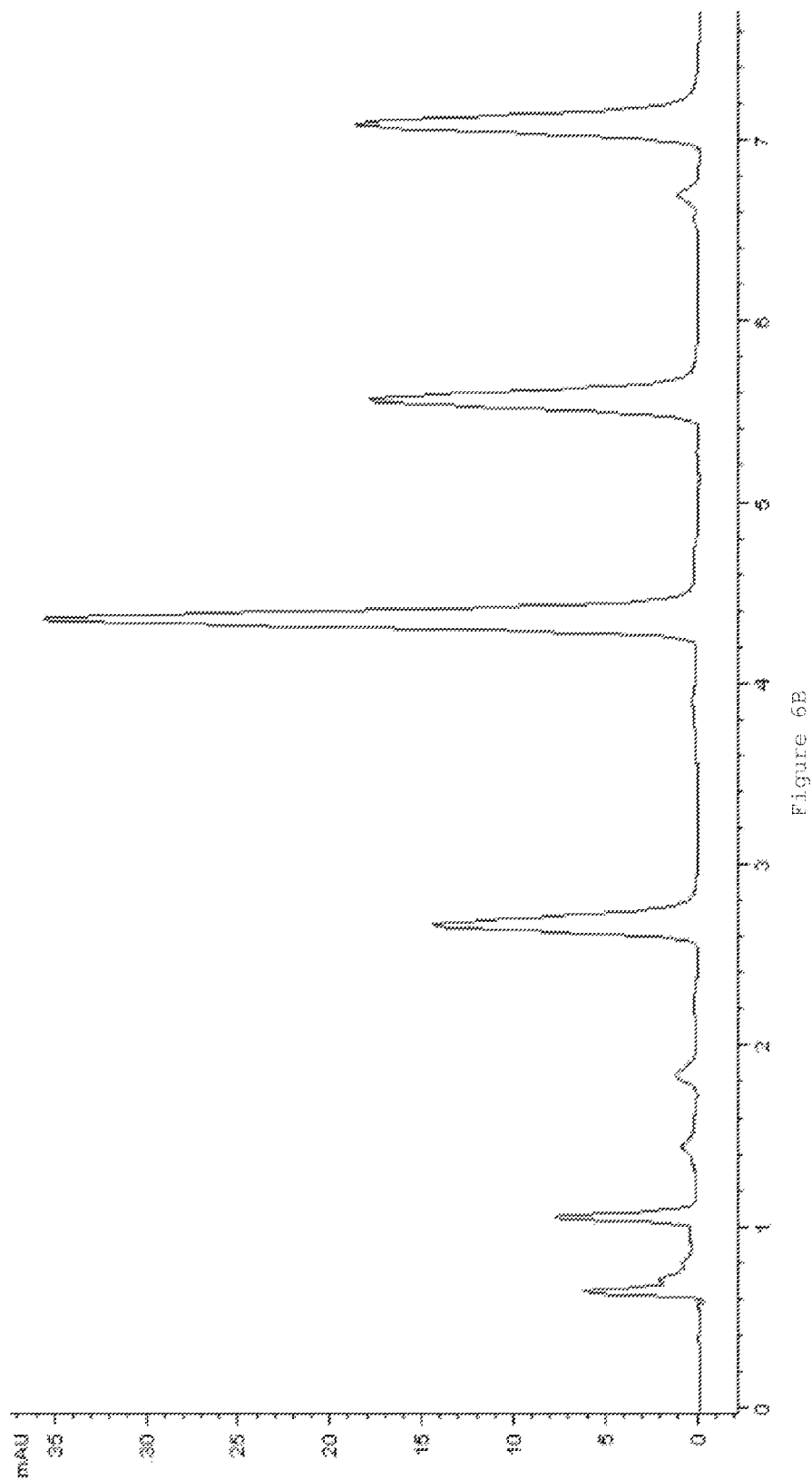
FIG. 6 shows an HPLC trace of the nucleosides obtained by digestion of a 15 bp DNA strand containing 5fC before (FIG. 6A) and after (FIG. 6B) bisulfite treatment.

Following bisulfite treatment, only a very small peak for 5fC remains, and negligible cytosine is present. The uracil peak in FIG. 6B is derived from the 5fC, as well as from deamination of unmodified C.

Figure 7A:
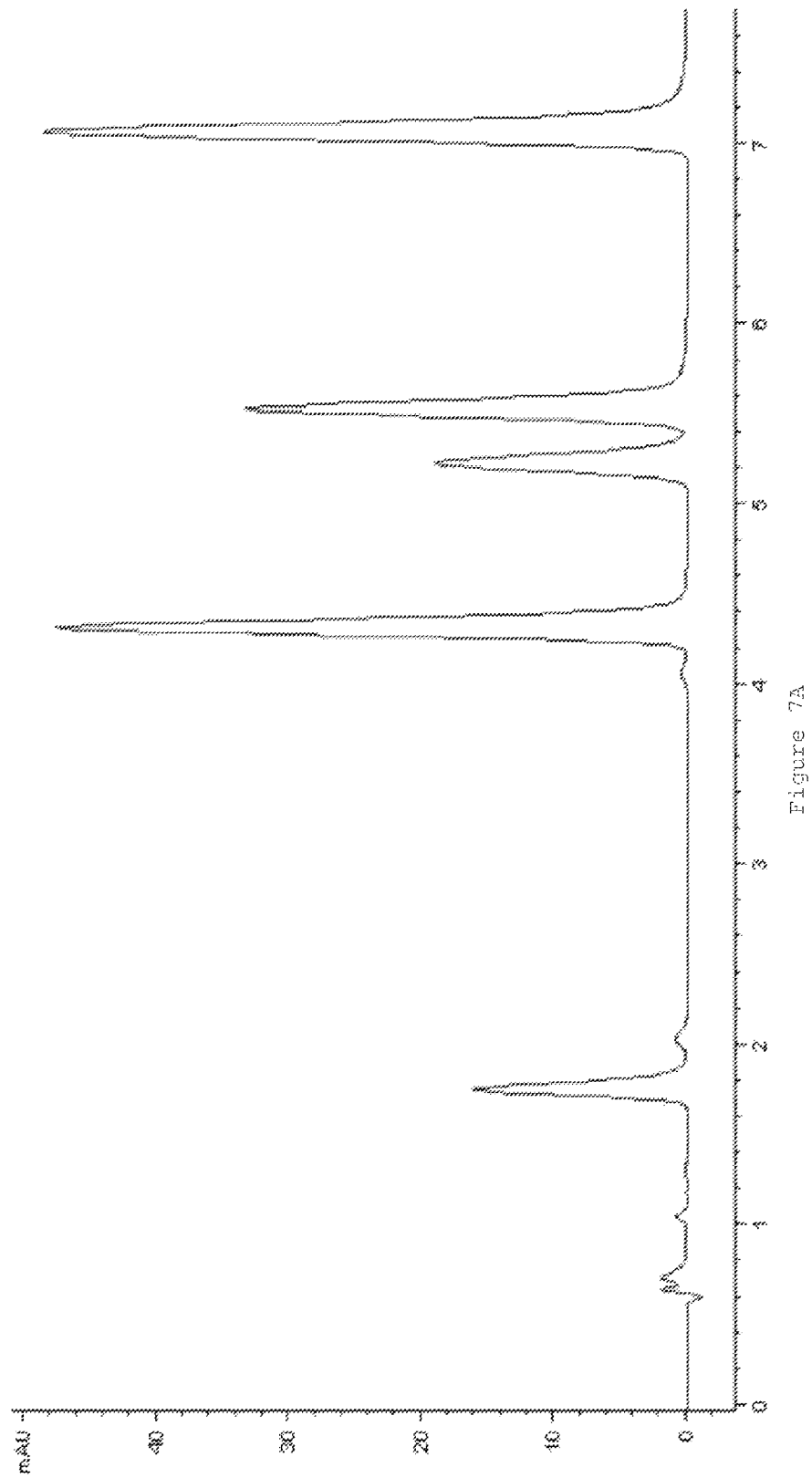
FIG. 7 shows an HPLC trace of the nucleosides obtained by digestion of a 140 bp DNA molecule containing 5fC before (FIG. 7A) and after (FIG. 7B) reduction.
Figure 7B:
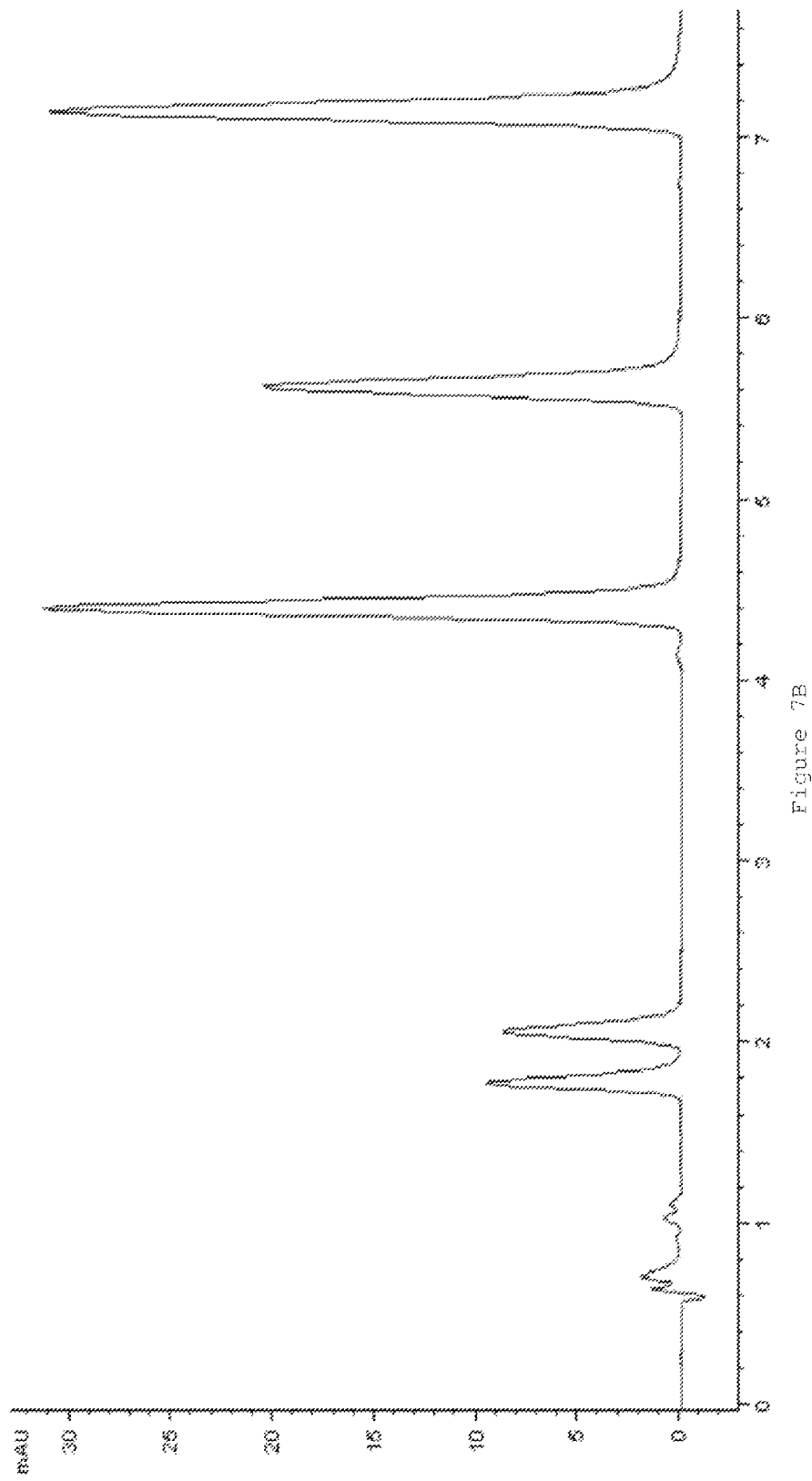

A 140 bp DNA molecule (SEQ ID NO: 1) was prepared which contained 45 5fC nucleosides incorporated through PCR. The DNA was reduced using NaBH4 as described above. Before and after reduction, samples of the DNA were digested to nucleosides with Benzonase, Phosphodiesterase I and Alkaline Phosphatase. This mixture of nucleosides was then injected into the HPLC, to give the traces shown in FIGS. 7A (before reduction) and 7B (after reduction). Complete conversion of 5fC to 5hmC was observed.

Oxidised bisulfite conversion of a ClaI site (ATCGAT) in a 122 base pair double stranded DNA (SEQ ID NO: 3) was investigated to test the efficiency and selectivity of the oxidative bisulfite method. A double stranded 122 base pair DNA fragment with a single CpG in the centre (in the context of a ClaI ATCGAT restriction site; SEQ ID NO: 3) was amplified by PCR using 5-methylcytosine primers and either CTP, 5mCTP or 5hmCTP. The amplified product contained 5-methylcytosine in the primer regions and CpG, 5mCpG, or 5hmCpG in the centre CpG.

As described above, the three synthetic 122mer dsDNAs containing either C, 5mC or 5hmC were each oxidised with $KRuO_4$ and then subjected to a conventional bisulfite conversion protocol. Sanger sequencing was carried out on each of the three strands (FIG. 8).

The C-containing strand completely converted to U (FIG. 8 LH panel), the 5mC-containing strand did not convert (FIG. 8 Middle panel) and the 5hmC containing strand converted almost quantitatively to U, with a trace of unconverted C (FIG. 8 RH panel). This shows up as a major adenine peak from the converted material, and the residual guanine peak arises from a minority of unconverted material.

To gain an accurate measure of the efficiency of conversion of 5hmC to U, Illumina sequencing was carried out on the synthetic strand containing 5hmC after oxidative bisulfite treatment. An overall 5hmC to U conversion level of 94.5% was observed (FIG. 3C). The oxidative bisulfite protocol was also applied to a second strand that contained multiple 5hmC residues in a range of different contexts and also showed similarly high conversion efficiency (94.7%) of 5hmC to U (FIG. 3C). Finally, the $KRuO_4$ oxidation was carried out on genomic DNA and showed a quantitative yield of 5hmC to 5fC conversion by mass spectrometry (FIG. 3D) with no significant degradation of C (FIG. 4C). These proof of principle experiments demonstrate that the oxidative bisulfite protocol will specifically convert 5hmC to U in DNA, leaving C and 5mC unchanged, allowing quantitative, single nucleotide resolution sequencing on widely available platforms (oxBS-Seq).

We then used the oxidative bisulfite principle to quantitatively map 5hmC at high resolution in the genomic DNA of mouse ES cells. We chose to combine oxidative bisulfite with reduced representation bisulfite sequencing (RRBS) (24), which allows for selective sequencing of a portion of the genome that is highly enriched for CpG islands (CGIs), thus ensuring adequate sequencing depth to detect this less abundant mark. We therefore generated RRBS and oxRRBS datasets, achieving an average sequencing depth of ~120 reads per CpG, which when pooled yielded an average of ~3,300 methylation calls per CGI. After applying depth and breadth cutoffs (see Materials and Methods), 55% (12, 660) of all CGIs (25) were covered in our datasets. Our RRBS (i.e., non-oxidised) data correlates well with published RRBS and BS-Seq datasets (24, 26).

To identify 5hmC-containing CGIs, we tested for differences between the RRBS and oxRRBS datasets using stringent criteria (see Materials and Methods). It was expected that most significant differences would stem from CGIs that had a lower proportion of unconverted cytosines in the oxRRBS set when compared with the RRBS set. CGIs that had the reverse trend were used to estimate a false discovery rate, which was 3.7% (FIG. 9A). We identified 800 5hmC-containing CGIs, which had an average of 3.3% (range 0.2-18.5%) CpG hydroxymethylation (FIGS. 9A and B). We also identified 4,577 5mC-containing CGIs averaging 8.1% CpG methylation (FIG. 9B). We carried out sequencing on an independent biological duplicate sample of the same ES cell line but at a different passage number, which by mass spectrometry had reduced levels of 5hmC (0.10% versus 0.16% of all Cs) and consistently we found fewer 5hmC-containing CGIs. Importantly, 5hmC-containing CGIs present in both samples showed good quantitative reproducibility.

To validate our method, we selected 21 CGIs containing MspI restriction sites and quantified 5hmC and 5mC levels at these CpGs by glucMS-qPCR (28) (FIG. 9D). We found a good correlation between the quantification by oxRRBS and glucMS-qPCR (r=0.86, p=5E-7 and r=0.52, p=0.01 for 5mC and 5hmC, respectively), Reduced bisulfite conversion (reBS-Seq) of DNA strand containing a 5-formylcytosine (5fC) was investigated.

A synthetic 100mer DNA strand (SEQ ID NO: 8) containing the sequence ACGGA5fCGTA was put through a reduction with NaBH4, and then subjected to a conventional bisulfite conversion protocol. Sanger sequencing was then carried out on the strand (FIG. 11).

FIG. 11 shows the sequencing trace that represents part of the reverse complement sequence (TACGTCCAT). The positions of the 5fC and C are in bold and shown in brackets on the template strand in FIG. 11. As previously shown, both 5fC and C deaminate under bisulfite conditions to form U, which shows as A in the reverse complement sequence of FIG. 11. However, reduction with NaBH4 converts 5fC to 5hmC, which is not deaminated into U, and shows as G in the reverse complement sequence of FIG. 11. Reduced Bisulfite Sequencing (redBS-Seq) therefore allows the discrimination of 5fC and C at single-base resolution.

In summary, we have shown that the oxBS-Seq method reliably maps and quantifies both 5mC and 5hmC at single nucleotide level. Oxidative bisulfite is also compatible with non-sequencing downstream approaches such as Sequenom, as demonstrated here. Therefore, by comparing the sequence of bisulfite treated and oxidised and bisulfite treated genomic DNA, it is possible to determine the presence of 5-methylcytosine and 5-hydroxymethylcytosine, along with the non-modified cytosine.

For example, uracil residues at the same position in the sequences of both bisulfite treated and oxidised and bisulfite treated genomic DNA indicate the presence of non-modified cytosine. Cytosine residues at the same position in the sequences of both bisulfite treated and oxidised and bisulfite treated genomic DNA indicate the presence of 5-methylcytosine. A cytosine residue in the sequence of the oxidised and bisulfite treated genomic DNA also indicates the presence of 5-methylcytosine. A cytosine residue in the sequence of the bisulfite treated genomic DNA and a uracil residue at the same position in the sequence of the oxidised and bisulfite treated genomic DNA indicates the presence of 5-hydroxymethylcytosine.

5-formylcytosine may also be sequenced to single nucleotide resolution. 5fC may be quantitatively reduced to hmC in genomic DNA using NaBH4 (as shown by HPLC). By comparing the sequence of untreated, bisulfite treated, oxidised and bisulfite treated and reduced and bisulfite treated genomic DNA, the presence of all three known cytosine mammalian modifications, 5-methylcytosine, 5-hydroxymethylcytosine and 5-formylcytosine, may be determined along with the non-modified cytosine. For example, uracil residues at the same position in the sequences of i) bisulfite treated, ii) oxidised and bisulfite treated and iii) reduced and bisulfite treated genomic DNA (UUU) indicate the presence of non-modified cytosine.

Cytosine residues at the same position in the sequences of i) bisulfite treated, ii) oxidised and bisulfite treated and iii) reduced and bisulfite treated genomic DNA (CCC) indicate the presence of 5-methylcytosine.

A cytosine residue in the sequence of the bisulfite treated genomic DNA; a uracil residue at the same position in the sequence of the oxidised and bisulfite treated genomic DNA and, optionally, a cytosine residue at the same position in the sequence of the reduced and bisulfite treated genomic DNA (CUC) indicates the presence of 5-hydroxymethylcytosine.

A uracil residue in the sequence of the bisulfite treated genomic DNA; a cytosine residue at the same position in the sequence of the reduced and bisulfite treated genomic DNA; and optionally, a uracil residue at the same position in the sequence of the oxidised and bisulfite treated genomic DNA (UCU) and indicates the presence of 5-formylcytosine.

Both modified and unmodified cytosines are read as cytosine when untreated genomic DNA is sequenced.

The HPLC chromatograms shown in FIG. 10 confirm that no significant degradation of RNA is observed following oxidation of a 28 nucleotide RNA strand (SEQ ID NO: 7). This result means that the oxidation approach is also compatible for sequencing modified cytosine residues, such as 5hmC, as described herein in RNA.

REFERENCES

1. A. M. Deaton et al *Genes Dev.* 25, 1010 (May 15, 2011).
2. M. Tahiliani et al. *Science* 324, 930 (May 15, 2009).
3. S. Ito et al. *Nature* 466, 1129 (Aug. 26, 2010).
4. A. Szwagierczak et al *Nucleic Acids Res,* (Aug. 4, 2010).
5. K. P. Koh et al. *Cell Stem Cell* 8, 200 (Feb. 4, 2011).
6. G. Ficz et al., *Nature* 473, 398 (May 19, 2011).
7. K. Williams et al. *Nature* 473, 343 (May 19, 2011).
8. W. A. Pastor et al. *Nature* 473, 394 (May 19, 2011).
9. Y. Xu et al. *Mol. Cell.* 42, 451 (May 20, 2011).
10. M. R. Branco et al *Nat. Rev. Genet.* 13, 7 (January, 2012).
11. S. Kriaucionis et al *Science* 324, 929 (May 15, 2009).
12. M. Munzel et al. *Angew. Chem. Int. Ed.* 49, 5375 (July 2010).
13. H. Wu et al. *Genes Dev.* 25, 679 (Apr. 1, 2011).
14. S. G. Jin et al *Nuc. Acids. Res.* 39, 5015 (July, 2011).
15. C. X. Song et al. *Nat. Biotechnol.* 29, 68 (January, 2011).
16. M. Frommer et al. *PNAS. U.S.A.* 89, 1827 (March 1992).
17. Y. Huang et al. *PLoS One* 5, e8888 (2010).
18. C. Nestor et al *Biotechniques* 48, 317 (April, 2010).
19. C. X. Song et al. *Nat. Methods,* (Nov. 20, 2011).
20. J. Eid et al. *Science* 323, 133 (Jan. 2, 2009).
21. E. V. Wallace et al. *Chem. Comm.* 46, 8195 (Nov. 21, 2010).
22. M. Wanunu et al. *J. Am. Chem. Soc.,* (Dec. 14, 2010).
23. G. Green, W et al *J Chem Soc Perk T* 1, 681 (1984).
24. A. Meissner et al. *Nature* 454, 766 (Aug. 7, 2008).
25. R. S. Illingworth et al. *PLoS genetics* 6, (September, 2010).
26. M. B. Stadler et al. *Nature* 480, 490 (Dec. 22, 2011).
27. J. Borgel et al et al *Nat. Genet.* 42, 1093 (December, 2010).
28. S. M. Kinney et al. *J. Biol. Chem.* 286, 24685 (Jul. 15, 2011).
29. N. Lane et al. *Genesis* 35, 88 (February, 2003).
30. E. P. Quinlivan et al 3rd, *Anal. Biochem.* 373, 383 (February 2008).
31. H. Gu et al. *Nat. Protoc.* 6, 468 (April, 2011).
32. F. Krueger et al *PLoS One* 6, e16607 (2011).
33. F. Krueger et al *Bioinformatics* 27, 1571 (Jun. 1, 2011).
34. S. A. Schichman et al *Mol. Biol. Evol.* 10, 552 (May, 1993).
35. J. L. Goodier et al. *Genome research* 11, 1677 (October, 2001).
36. C. Qin et al. *Mol. Carcinog.* 49, 54 (January, 2010).
37. Li et al *Nucleic Acids* (2011) Article ID 870726
38. Pfaffeneder, T. et al (2011) *Angewandte.* 50. 1-6
39. Lister, R. et al (2008) *Cell.* 133. 523-536
40. Wang et al (1980) Nucleic Acids Research. 8 (20), 4777-4790
41. Hayatsu et al (2004) *Nucleic Acids Symposium Series No.* 48 (1), 261-262
42. Lister et al (2009) Nature. 462. 315-22
43. Sanger, F. et al PNAS USA, 1977, 74, 5463
44. Bentley et al Nature, 456, 53-59 (2008)
45. K J McKernan et al Genome Pes. (2009) 19: 1527-1541
46. M Ronaghi et al Science (1998) 281 5375 363-365
47. Eid et al Science (2009) 323 5910 133-138
48. Korlach et al Methods in Enzymology 472 (2010) 431-455)
49. Rothberg et al (2011) Nature 475 348-352).

```
Model Sequences 140 base pair double stranded DNA model (SEQ ID NO: 1):
CACATCCCACACTATACACTCATACATACCTGCTCACGACGACGCTGTACACCTACGTACTCGTGCACGCTCGTC
ACGTGATCGACCATGACTCTGACGCACTGAGGTATGGGAAGTAGTGAGTAGATTGTAGTAAGGAG 15 nucleotide long single stranded DNA model (SEQ ID NO: 2):
GAGACGACGTACAGG 122 base pair double stranded DNA model (SEQ ID NO: 3):
CACATCCCACACTATACACTCATACATACCATTTAAATAAATTAAATAATATTAATATATCGATTAATAATAAAT
AATAATTAATTAATATTGGGAAGTAGTGAGTAGATTGTAGTAAGGAG 135 base pair double stranded DNA model (SEQ ID NO: 4):
CACATCCCACACTATACACTCATACATACCATTTAACGATAAATTACAATAACGTATCTAATCATATCGATAAC
TAATCGAAATAATAATTACGCATTAATATTGGGAAGTAGTGAGTAGATTGTAGTAAGGAG dsDNA fwd primer (SEQ ID NO: 5):
CACATCCCACACTATACACTCATACATACC dsDNA rev primer (SEQ ID NO: 6):
CTCCTTACTACAATCTACTCACTACTTCCC 28 nucleotide RNA model sequence (SEQ ID NO: 7):
UGUGGGGAGGGCGGGGCGGGGUCUGGGG 100 nucleotide 5fC containing sequence (SEQ ID NO: 8):
[5fC position indicated by bold, italics]
GACGGA*C*GTACGATCGAGCGAGGTCTTGGGTCAGCAGGTGGCGACTGTTAGCTCAGATGGCTAGCAAGTGGGTAT
GTATGAGTGTATAGTGTGGGATGTG
```

Modified nucleotides are in bold italics

TABLE 1

| Base | Regular Sequencing | Bisulfite Sequencing | Oxidation then Bisulfite Sequencing | Reduction then Bisulfite Sequencing |
|---|---|---|---|---|
| C | C | U | U | U |
| 5mC | C | C | C | C |
| 5hmC | C | C | U | C |
| 5fC | C | U | U | C |

TABLE 2

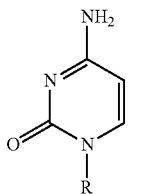 a)

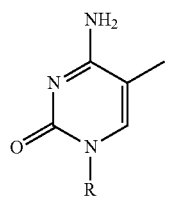 b)

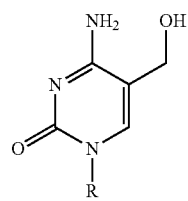 c)

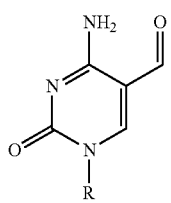 d)

TABLE 3

| Oxidant | Comment |
| --- | --- |
| $KRuO_4$ | Complete conversion to aldehyde |
| $CrO_3$ | No oxidation observed |
| PDC | No oxidation observed |
| PCC | No oxidation observed |
| $MnO_2$ | Small amount of aldehyde observed but substantial degradation with excess oxidant |

TABLE 4

Retention Times for HPLC Peaks (DNA)

| Base | Retention Time/min |
| --- | --- |
| C | 1.8 |
| 5hmC | 2.1 |
| U | 2.7 |
| G | 4.5 |
| 5fC | 5.3 |
| T | 5.7 |
| A | 7.3 |

TABLE 5

Retention Times for HPLC Peaks (RNA)

| Base | Retention Time/min |
| --- | --- |
| C | 1.3 |
| U | 1.8 |
| G | 3.7 |
| A | 6.7 |

---

The invention claimed is:

1. A method of identifying a modified cytosine residue in a sample nucleotide sequence comprising the steps of:
   (i) providing a population of polynucleotides which comprise the sample nucleotide sequence,
   (ii) oxidising or reducing a first portion of said population,
   (iii) treating the oxidised or reduced first portion of said population and a second portion of said population with bisulfite,
   (iv) sequencing the polynucleotides in the first and second portions of the population following steps (ii) and (iii) to produce first and second nucleotide sequences, respectively, and
   (v) identifying a residue in the first and second nucleotide sequences which corresponds to a cytosine residue in the sample nucleotide sequence.

2. A method according to claim 1 wherein the modified cytosine residue is 5-methylcytosine, 5-hydroxymethylcytosine or 5-formylcytosine.

3. A method according to claim 1 wherein the first portion of said population is oxidised in step (ii).

4. A method according to claim 3 wherein said oxidation selectively oxidises 5-hydroxymethylcytosine residues.

5. A method according to claim 3 wherein step (ii) comprises multiple steps of oxidation of the first portion of said population.

6. A method according to claim 3 wherein the first portion is oxidised using a chemical oxidising agent.

7. A method according to claim 3 wherein the first portion is oxidised using a perruthenate oxidising agent.

8. A method according to claim 3 wherein the first portion is oxidised using $KRuO_4$.

9. A method according to claim 3 wherein identification of uracil at a position in the first nucleotide sequence which corresponds to a cytosine residue in the sample nucleotide sequence and cytosine at the same position in the second nucleotide sequence is indicative that the cytosine residue in the sample nucleotide sequence is 5-hydroxylmethylcytosine.

10. A method according to claim 3 wherein identification of cytosine at a position in both the first and second nucleotide sequences which corresponds to a cytosine residue in the sample nucleotide sequence is indicative that the cytosine residue in the sample nucleotide sequence is 5-methylcytosine.

11. A method according to claim 3 wherein identification of cytosine at a position in the first nucleotide sequence which corresponds to a cytosine residue in the sample nucleotide sequence is indicative that the cytosine residue in the sample nucleotide sequence is 5-methylcytosine.

12. A method according to claim 3 further comprising the steps of:
   (vi) reducing a third portion of the population of polynucleotides comprising the sample nucleotide sequence,
   (vii) treating the reduced third portion of the population with bisulfite,
   (viii) sequencing the polynucleotides in the third portion following steps (vi) and (vii) to produce a third nucleotide sequence, and
   (ix) identifying a residue in the third nucleotide sequence which corresponds to a cytosine residue in the sample nucleotide sequence.

13. A method according to claim 12 wherein identification of uracil at a position in the first and second nucleotide sequences which corresponds to a cytosine residue in the sample nucleotide sequence and a cytosine at this position in the third nucleotide sequence is indicative that the cytosine residue in the sample nucleotide sequence is 5-formylcytosine.

14. A method according to claim 1 wherein the first portion of said population is reduced in step (ii).

15. A method according to claim 14 wherein the first portion of said population is reduced using $NaBH_4$.

16. A method according to claim 14 wherein identification of cytosine at a position in the first nucleotide sequence which corresponds to a cytosine residue in the sample nucleotide sequence and uracil at the same position in the second nucleotide sequence is indicative that the cytosine residue in the sample nucleotide sequence is 5-formylcytosine.

17. A method according to claim 14 wherein identification of uracil at a position in both the first and the second nucleotide sequence which corresponds to a cytosine residue in the sample nucleotide sequence is indicative that the cytosine residue in the sample nucleotide sequence is unmodified cytosine.

18. A method according to claim 12 comprising;
   providing a fourth portion of the population of polynucleotides comprising the sample nucleotide sequence; and,
   sequencing the polynucleotides in the fourth portion to produce the sample nucleotide sequence.

19. A method of identifying 5-methylcytosine in a sample nucleotide sequence comprising the steps of:
   (i) providing a population of polynucleotides which comprise the sample nucleotide sequence,
   (ii) oxidising said population of polynucleotides,
   (iii) treating the oxidised population of polynucleotides with bisulfite to generate an oxidised, bisulfite treated population of polynucleotides,
   (iv) sequencing the polynucleotides in the oxidised, bisulfite treated population to produce a treated nucleotide sequence, and
   (v) identifying a residue in the treated nucleotide sequence which corresponds to a cytosine residue in the sample nucleotide sequence,
   wherein the presence of a cytosine in the treated nucleotide sequence is indicative that the cytosine residue in the sample nucleotide sequence is 5-methylcytosine.

20. A method according to claim 1 wherein the polynucleotides are genomic DNA.

21. A method according to claim 20 wherein the genomic DNA is mammalian genomic DNA.

22. A method according to claim 1 wherein the polynucleotides are RNA.

23. A method according to claim 22 wherein the RNA is genomic RNA, mRNA, tRNA, rRNA or non-coding RNA.

24. A method according to claim 23 wherein the genomic RNA is mammalian, plant or viral genomic RNA.

25. A method according to claim 18 wherein the population of polynucleotides or one or more of the first, second, third and fourth portions of the population are immobilised.

26. A method according to claim 18 wherein one or more of the first, second, third and fourth portions of the population are amplified before sequencing.

27. A method according to claim 26 wherein one or more of the first, second, and third portions of the population are amplified following treatment with bisulfite.

* * * * *

SEQUENCE LISTING

<160> NUMBER OF SEQ ID NOS: 8

<210> SEQ ID NO 1
<211> LENGTH: 140
<212> TYPE: DNA
<213> ORGANISM: Artificial Sequence
<220> FEATURE:
<223> OTHER INFORMATION: Synthetic sequence: 140 base pair double
      stranded DNA model

<400> SEQUENCE: 1
cacatcccac actatacact catacatacc tgctcacgac gacgctgtac acctacgtac     60
tcgtgcacgc tcgtcacgtg atcgaccatg actctgacgc actgaggtat gggaagtagt    120
gagtagattg tagtaaggag                                                 140

<210> SEQ ID NO 2
<211> LENGTH: 15
<212> TYPE: DNA
<213> ORGANISM: Artificial Sequence
<220> FEATURE:
<223> OTHER INFORMATION: Synthetic sequence: 15 nucleotide long single
      stranded DNA model

<400> SEQUENCE: 2
gagacgacgt acagg                                                      15

<210> SEQ ID NO 3
<211> LENGTH: 122
<212> TYPE: DNA
<213> ORGANISM: Artificial Sequence
<220> FEATURE:
<223> OTHER INFORMATION: Synthetic sequence: 122 base pair double
      stranded DNA model

<400> SEQUENCE: 3
cacatcccac actatacact catacatacc atttaaataa attaaataat attaatatat     60
cgattaataa taaataataa ttaattaata ttgggaagta gtgagtagat tgtagtaagg    120
ag                                                                  122

<210> SEQ ID NO 4
<211> LENGTH: 135
<212> TYPE: DNA
<213> ORGANISM: Artificial Sequence
<220> FEATURE:
<223> OTHER INFORMATION: Synthetic sequence: 135 base pair double
      stranded DNA model

<400> SEQUENCE: 4
cacatcccac actatacact catacatacc atttaacgat aaattacaat aacgtatcta     60
atcatatcga ttaactaatc gaaataataa ttacgcatta atattgggaa gtagtgagta    120
gattgtagta aggag                                                    135

<210> SEQ ID NO 5
<211> LENGTH: 30
<212> TYPE: DNA
<213> ORGANISM: Artificial Sequence
<220> FEATURE:
<223> OTHER INFORMATION: Synthetic sequence: dsDNA fwd primer

<400> SEQUENCE: 5
cacatcccac actatacact catacatacc                                     30

<210> SEQ ID NO 6
<211> LENGTH: 30
<212> TYPE: DNA
<213> ORGANISM: Artificial Sequence
<220> FEATURE:
<223> OTHER INFORMATION: Synthetic sequence: dsDNA rev primer

<400> SEQUENCE: 6
ctccttacta caatctactc actacttccc                                     30

<210> SEQ ID NO 7
<211> LENGTH: 28
<212> TYPE: RNA
<213> ORGANISM: Artificial Sequence
<220> FEATURE:
<223> OTHER INFORMATION: Synthetic sequence: 28 nucleotide RNA model
      sequence

<400> SEQUENCE: 7
uguggggagg gcggggcggg gucugggg                                       28

<210> SEQ ID NO 8
<211> LENGTH: 100
<212> TYPE: DNA
<213> ORGANISM: Artificial Sequence
<220> FEATURE:
<223> OTHER INFORMATION: Synthetic sequence: 100 nucleotide 5fC
      containing sequence

```
<220> FEATURE:
<221> NAME/KEY: misc_feature
<222> LOCATION: (7)..(7)
<223> OTHER INFORMATION: n is 5-formylcytosine

<400> SEQUENCE: 8
gacggangta cgatcgagcg aggtcttggg tcagcaggtg gcgactgtta gctcagatgg      60
ctagcaagtg ggtatgtatg agtgtatagt gtgggatgtg                          100
```